(12) United States Patent
Jones et al.

(10) Patent No.: US 11,324,744 B2
(45) Date of Patent: May 10, 2022

(54) METHODS OF USE AND PHARMACEUTICAL COMBINATIONS OF HISTONE DEACETYLASE INHIBITORS AND CD20 INHIBITORY ANTIBODIES

(71) Applicant: Acetylon Pharmaceuticals Inc., Boston, MA (US)

(72) Inventors: Simon Steward Jones, Harvard, MA (US); Chengyin Min, Brookline, MA (US); Steven Norman Quayle, Brookline, MA (US)

(73) Assignee: Acetylon Pharmaceuticals Inc., Boston, MA (US)

( * ) Notice: Subject to any disclaimer, the term of this patent is extended or adjusted under 35 U.S.C. 154(b) by 0 days.

(21) Appl. No.: 15/670,743

(22) Filed: Aug. 7, 2017

(65) Prior Publication Data
US 2018/0036306 A1    Feb. 8, 2018

Related U.S. Application Data

(60) Provisional application No. 62/372,093, filed on Aug. 8, 2016.

(51) Int. Cl.
| | |
|---|---|
| *A61K 31/505* | (2006.01) |
| *A61K 45/06* | (2006.01) |
| *A61K 39/395* | (2006.01) |
| *A61P 35/00* | (2006.01) |
| *A61K 9/00* | (2006.01) |
| *C07K 16/28* | (2006.01) |
| *A61K 39/00* | (2006.01) |

(52) U.S. Cl.
CPC .......... *A61K 31/505* (2013.01); *A61K 9/0019* (2013.01); *A61K 9/0053* (2013.01); *A61K 39/3955* (2013.01); *A61K 39/39558* (2013.01); *A61K 45/06* (2013.01); *A61P 35/00* (2018.01); *C07K 16/2887* (2013.01); *A61K 2039/505* (2013.01); *A61K 2039/54* (2013.01); *C07K 2317/24* (2013.01); *C07K 2317/56* (2013.01); *C07K 2317/565* (2013.01); *C07K 2317/76* (2013.01)

(58) Field of Classification Search
CPC ............ A61K 31/505; A61K 2039/505; A61K 2300/00; A61K 39/001124; A61K 2039/54; A61K 45/06; C07K 2317/76; C07K 16/2887
See application file for complete search history.

(56) References Cited

U.S. PATENT DOCUMENTS

| | | |
|---|---|---|
| 6,777,217 B1 | 8/2004 | Schreiber et al. |
| 7,244,853 B2 | 7/2007 | Schreiber et al. |
| 7,250,504 B2 | 7/2007 | Grozinger et al. |
| 7,994,362 B2 | 8/2011 | Schreiber et al. |
| 8,148,526 B1 | 4/2012 | Van Duzer et al. |
| 8,394,810 B2 | 3/2013 | Van Duzer et al. |
| 8,609,678 B2 | 12/2013 | Van Duzer et al. |
| 8,614,223 B2 | 12/2013 | Van Duzer et al. |
| 8,999,289 B2 | 4/2015 | Anderson et al. |
| 9,096,549 B2 | 8/2015 | Van Duzer et al. |
| 9,139,583 B2 | 9/2015 | Van Duzer et al. |
| 9,145,412 B2 | 9/2015 | Van Duzer et al. |
| 9,278,963 B2 | 3/2016 | Van Duzer et al. |
| 9,421,212 B2 | 3/2016 | Van Duzer et al. |
| 9,403,779 B2 | 8/2016 | Tamang et al. |
| 9,409,890 B2 | 8/2016 | Van Duzer et al. |
| 9,464,073 B2 | 10/2016 | Mazitschek et al. |
| 9,562,013 B2 | 2/2017 | Van Duzer et al. |
| 9,663,825 B2 | 5/2017 | Yang et al. |
| 2004/0266769 A1 | 12/2004 | Bressi et al. |
| 2005/0119305 A1 | 6/2005 | Naka et al. |
| 2006/0239909 A1 | 10/2006 | Anderson et al. |
| 2007/0093413 A1 | 4/2007 | Schreiber et al. |
| 2007/0149495 A1 | 6/2007 | Bressi et al. |
| 2009/0023786 A1 | 1/2009 | Miller et al. |
| 2009/0209590 A1 | 8/2009 | Mazitschek et al. |
| 2009/0305384 A1 | 12/2009 | Grozinger et al. |
| 2009/0312363 A1 | 12/2009 | Bradner et al. |
| 2010/0137196 A1 | 6/2010 | Schreiber et al. |
| 2010/0330197 A1 | 12/2010 | Higashiguchi et al. |
| 2011/0218154 A1 | 9/2011 | Schreiber et al. |
| 2013/0225543 A1 | 8/2013 | Jones et al. |
| 2014/0011767 A1 | 1/2014 | Yang et al. |

(Continued)

FOREIGN PATENT DOCUMENTS

| | | |
|---|---|---|
| WO | 2001/070675 A2 | 9/2001 |
| WO | 2002/074298 A1 | 9/2002 |

(Continued)

OTHER PUBLICATIONS

Abstractor Hamlin et al, Blood, Dec. 2015, vol. 126, No. 23 (Year: 2015).*
Santo et al (Blood, 2012, vol. 119, pp. 2579-2589) (Year: 2012).*
Mao et al (PLOS One, 2013, vol. 8, Issue 11, e80533) (Year: 2013).*
Damm et al. (Experimental Hematology and Oncology, 2015, vol. 4, 1-7 pages) (Year: 2015).*
Singh et al., Journal of Cancer Science and Therapy, 2015, vol. 7, pp. 347-358 (Year: 2015).*
Biosis Database [Online] Record for Bobrowicz et al. (Jun. 26, 2017) "HDAC6 Inhibition Sensitizes Tumor Cells to Anti-CD20 Immunotherapy In Vivo," Haematologica. 102(Suppl 2):568. Accession No. PREV201700644010.

(Continued)

*Primary Examiner* — Karen A. Canella
(74) *Attorney, Agent, or Firm* — Lathrop GPM LLP; Brian Trinque

(57) ABSTRACT

The disclosure relates to pharmaceutical combinations comprising an HDAC6 selective inhibitor and a CD20 inhibitory antibody for the treatment of a B-cell disorder, such as cancer, in a subject in need thereof. Also provided herein are methods for treating a B-cell disorder in a subject in need thereof, comprising administering to the subject an effective amount of an HDAC6 selective inhibitor and a CD20 inhibitory antibody.

13 Claims, 7 Drawing Sheets
Specification includes a Sequence Listing.

(56) References Cited

U.S. PATENT DOCUMENTS

| | | | |
|---|---|---|---|
| 2014/0142104 | A1 | 5/2014 | Van Duzer et al. |
| 2014/0142117 | A1 | 5/2014 | Van Duzer et al. |
| 2014/0357512 | A1 | 12/2014 | Yang et al. |
| 2015/0045380 | A1 | 2/2015 | Van Duzer et al. |
| 2015/0099744 | A1 | 4/2015 | Yang et al. |
| 2015/0105358 | A1 | 4/2015 | Quayle et al. |
| 2015/0105383 | A1 | 4/2015 | Quayle et al. |
| 2015/0105384 | A1 | 4/2015 | Jones et al. |
| 2015/0105409 | A1 | 4/2015 | Quayle et al. |
| 2015/0119413 | A1 | 4/2015 | Gradilone et al. |
| 2015/0150871 | A1 | 6/2015 | Quayle et al. |
| 2015/0176076 | A1 | 6/2015 | Yang et al. |
| 2015/0239869 | A1 | 8/2015 | Mazitschek et al. |
| 2015/0250786 | A1 | 9/2015 | Berton et al. |
| 2015/0299130 | A1 | 10/2015 | Van Duzer et al. |
| 2015/0359794 | A1 | 12/2015 | Benz et al. |
| 2016/0030458 | A1 | 2/2016 | Jones et al. |
| 2016/0137630 | A1 | 5/2016 | Shearstone et al. |
| 2016/0158231 | A1 | 6/2016 | Jarpe et al. |
| 2016/0158232 | A1 | 6/2016 | Pozzi et al. |
| 2016/0168093 | A1 | 6/2016 | Van Duzer et al. |
| 2016/0228434 | A1 | 8/2016 | Reilly et al. |
| 2016/0279128 | A1 | 9/2016 | Van Duzer et al. |
| 2016/0339022 | A1 | 11/2016 | Tamang et al. |
| 2016/0346279 | A1 | 12/2016 | Kavelaars et al. |
| 2016/0355486 | A1 | 12/2016 | Seyedi et al. |
| 2016/0375021 | A1 | 12/2016 | Van Duzer et al. |
| 2017/0001965 | A1 | 1/2017 | Van Duzer et al. |
| 2017/0020872 | A1 | 1/2017 | Tamang et al. |
| 2017/0044144 | A1 | 2/2017 | Van Duzer et al. |
| 2017/0096403 | A1 | 4/2017 | Van Duzer et al. |
| 2017/0096413 | A1 | 4/2017 | Mazitschek et al. |

FOREIGN PATENT DOCUMENTS

| | | | |
|---|---|---|---|
| WO | 2003/037869 | A1 | 5/2003 |
| WO | 2006/102557 | A2 | 9/2006 |
| WO | 2007/014238 | A2 | 2/2007 |
| WO | 2007/022638 | A1 | 3/2007 |
| WO | 2007/130429 | A2 | 11/2007 |
| WO | 2007/144341 | A1 | 12/2007 |
| WO | 2008/003801 | A1 | 1/2008 |
| WO | 2008/033746 | A2 | 3/2008 |
| WO | 2008/091349 | A1 | 7/2008 |
| WO | 2010/011296 | A2 | 1/2010 |
| WO | 2010/131922 | A2 | 11/2010 |
| WO | 2011/019393 | A2 | 2/2011 |
| WO | 2011/084991 | A2 | 7/2011 |
| WO | 2011/091213 | A2 | 7/2011 |
| WO | 2011/146855 | A1 | 11/2011 |
| WO | 2013/013113 | A2 | 1/2013 |

OTHER PUBLICATIONS

Bobrowicz et al. (Dec. 1, 2014) "HDAC Inhibitors as Potential New Agents Improving the Efficacy of Monoclonal Antibodies," Blood. vol. 124. No. 21. Abstract No. 3641.

Bobrowicz et al. (Jun. 2014) "HDAC6 Inhibition Augments the Efficacy of Anti-CD20 Monoclonal Antibodies by Up-Regulating CD20 Level in Malignant B-Cells," Haematologica. 99(Suppl 1):437. Abstract No. P1143.

Bobrowicz et al. (Jan. 1, 2013) "HDAC6 Inhibition Increases CD20 Level and Improves the Efficacy of Anti-CD20 Monoclonal Antibodies," vol. 122. Abstract No. 4406.

Bobrowicz et al. (Jun. 26, 2017) "HDAC6 Inhibition Sensitizes Tumor Cells to Anti-CD20 Immunotherapy In Vivo," Haematologica. 102(Suppl 2):568. Abstract No. E1385.

Butler et al. (2000) "Suberoylanilide hydroxamic acid, an inhibitor of histone deacetylase, suppresses the growth of prostate cancer cells in vitro and in vivo," Cancer Res. 60:5165-5170.

Costello et al. (Dec. 2012) "Evidence for Changes in RREB-1, ZIP3, and Zinc in the Early Development of Pancreatic Adenocarcinoma," J. Gastrointest. Canc. 43:570-578.

Dokmanovic et al. (2007) "Histone Deacetylase Inhibitors: Overview and Perspectives," Mol. Cancer Res. 5 (10):981-989.

Giannini et al. (Jul. 2012) "Histone Deacetylase Inhibitors in the Treatment of Cancer: Overview and Perspectives," Future Med. Chem. 4(11):1439-1460.

Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.

Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.

Lane et al. (2009) "Histone Deacetylase Inhibitors in Cancer Therapy," J. Clin. Oncol. 27:5459-5468.

Loudni et al. (2007) "Design, synthesis and biological evaluation of 1, 4-benzodiazepine-2, 5-dione-based HDAC inhibitors," Bioorganic and Medicinal Chemistry Letters. 17:4819-4823.

Mazitschek et al. (2008) "Development of a Fluorescence Polarization Based Assay for Histone Deacetylase Ligand Discovery," Bioorganic and Medicinal Chemistry Letters. 18(9):2809-2812.

Miller et al. (1998) "Paclitaxel as the Initial Treatment of Multiple Myeloma: An Eastern Cooperative Oncology Group Study (E1A93)," Am. J. Clin. Oncol. 21(6):553-556.

Perez (1998) "Paclitaxel in Breast Cancer," The Oncologist. 3:373-389.

Ropero et al. (2007) "The Role of Histone Deacetylases (HDACs) in Human Cancer," Molecular Oncology. 1:19-25.

Smil et al. (2009) "Novel HDAC6 Isoform Selective Chiral Small Molecule Histone Deacetylase Inhibitors," Bioorganic and Medicinal Chemistry Letters. 19:688-692.

Sporn et al. (2000) "Chemoprevention of Cancer," Carcinogenesis. 21(3):525-530.

Thoppil et al. (Sep. 2011) "Terpenoids as Potential Chemopreventive and Therapeutic Agents in Liver Cancer," World J. Hepatol. 3(9):228-249.

International Search Report with Written Opinion corresponding to International Patent Application No. PCT/US2011/021982, dated Oct. 12, 2011.

International Search Report with Written Opinion corresponding to International Patent Application No. PCT/US2017/045751, dated Oct. 20, 2017.

Search Opinion corresponding to European Patent No. 11735212, dated Jun. 26, 2014.

Written Opinion corresponding to Singapore Patent Application No. Application No. 201205393-0, dated Nov. 15, 2013.

Niesvizky et al. "ACY-241, a Novel, HDAC6 Selective Inhibitor: Synergy with Immunomodulatory (IMiD?) Drugs in Multiple Myeloma (MM) Cells and Early Clinical Results (ACE-MM-200 Study)," 57th American Society of Hematology Annual Meeting and Exposition, Dec. 6, 2015, Orlando, FL, Session 653, No. 3040, Oral Presentation Abstract.

* cited by examiner

SEQUENCE LISTING

```
<160> NUMBER OF SEQ ID NOS: 68

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 1

Gly Tyr Thr Phe Thr Ser Tyr
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      heavy chain complementarity determining region
```

```
<400> SEQUENCE: 2

Tyr Pro Gly Asn Gly Asp
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 3

Ser Thr Tyr Tyr Gly Gly Asp Trp Tyr Phe Asn Val
1               5                   10

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 4

Ser Ser Val Ser Tyr Ile His
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 5

Ala Thr Ser Asn Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 6

Gln Gln Trp Thr Ser Asn Pro Pro Thr
1               5

<210> SEQ ID NO 7
<211> LENGTH: 125
<212> TYPE: PRT
<213> ORGANISM: Artificial Sequence
<220> FEATURE:
<223> OTHER INFORMATION: Description of Artificial Sequence: Synthetic
      heavy chain variable region

<400> SEQUENCE: 7

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
```

Ser Ile Ile Gly Thr Gly Gly Val Thr Tyr Tyr Ala Asp Ser Val Lys
            35                  40                  45
Ser Ile Ile Gly Thr Gly Gly Val Thr Tyr Tyr Ala Asp Ser Val Lys
        50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
        115                 120                 125

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable region

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 9
<211> LENGTH: 451
<212> TYPE: PRT
<213> ORGANISM: Artificial Sequence
<220> FEATURE:
<223> OTHER INFORMATION: Description of Artificial Sequence: Synthetic
      heavy chain complete

<400> SEQUENCE: 9

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly 100                 105                 110
Ala Gly Thr Thr Val Thr Val Ser Ala Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Ala Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 213
<212> TYPE: PRT
<213> ORGANISM: Artificial Sequence
<220> FEATURE:
<223> OTHER INFORMATION: Description of Artificial Sequence: Synthetic
      light chain complete

<400> SEQUENCE: 10

-continued

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 11

Gly Phe Thr Phe Asn Asp Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 12

Ser Trp Asn Ser Gly Ser
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      heavy chain complementarity determining region
```

```
<400> SEQUENCE: 13

Asp Ile Gln Tyr Gly Asn Tyr Tyr Gly Met Asp Val
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 14

Gln Ser Val Ser Ser Tyr Leu Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 15

Asp Ala Ser Asn Arg Ala Thr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 16

Gln Gln Arg Ser Asn Trp Pro Ile Thr
1               5

<210> SEQ ID NO 17
<211> LENGTH: 141
<212> TYPE: PRT
<213> ORGANISM: Artificial Sequence
<220> FEATURE:
<223> OTHER INFORMATION: Description of Artificial Sequence: Synthetic
      heavy chain variable region

<400> SEQUENCE: 17

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asn Asp Tyr Ala Met His Trp Val Arg Gln Ala Pro Gly Lys Gly Leu
    50                  55                  60

Glu Trp Val Ser Thr Ile Ser Trp Asn Ser Gly Ser Ile Gly Tyr Ala
65                  70                  75                  80

Asp Ser Val Lys Gly Arg Phe Thr Ile Ser Arg Asp Asn Ala Lys Lys
                85                  90                  95

Ser Leu Tyr Leu Gln Met Asn Ser Leu Arg Ala Glu Asp Thr Ala Leu
            100                 105                 110
```

Tyr Tyr Cys Ala Lys Asp Ile Gln Tyr Gly Asn Tyr Tyr Gly Met
            115                 120                 125

Asp Val Trp Gly Gln Gly Thr Thr Val Thr Val Ser Ser
        130                 135                 140

<210> SEQ ID NO 18
<211> LENGTH: 127
<212> TYPE: PRT
<213> ORGANISM: Artificial Sequence
<220> FEATURE:
<223> OTHER INFORMATION: Description of Artificial Sequence: Synthetic
      light chain variable region

<400> SEQUENCE: 18

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Ile Thr Phe Gly Gln Gly Thr Arg Leu Glu Ile Lys
        115                 120                 125

<210> SEQ ID NO 19
<211> LENGTH: 222
<212> TYPE: PRT
<213> ORGANISM: Artificial Sequence
<220> FEATURE:
<223> OTHER INFORMATION: Description of Artificial Sequence: Synthetic
      heavy chain complete

<400> SEQUENCE: 19

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Gly Ser Ser Lys Ser Thr Ser Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro
        210                 215                 220

<210> SEQ ID NO 20
<211> LENGTH: 211
<212> TYPE: PRT
<213> ORGANISM: Artificial Sequence
<220> FEATURE:
<223> OTHER INFORMATION: Description of Artificial Sequence: Synthetic
      light chain complete

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg
    210

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 21

Gly Tyr Ala Phe Ser Tyr Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 22

Phe Pro Gly Asp Gly Asp
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 23

Asn Val Phe Asp Gly Tyr Trp Leu Val Tyr
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 24

Lys Ser Leu Leu His Ser Asn Gly Ile Thr Tyr Leu Tyr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 25

Gln Met Ser Asn Leu Val Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 26

Ala Gln Asn Leu Glu Leu Pro Tyr Thr
1               5

<210> SEQ ID NO 27
<211> LENGTH: 120
<212> TYPE: PRT
<213> ORGANISM: Artificial Sequence
<220> FEATURE:

<223> OTHER INFORMATION: Description of Artificial Sequence: Synthetic
      heavy chain variable region

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala
        115                 120

<210> SEQ ID NO 28
<211> LENGTH: 113
<212> TYPE: PRT
<213> ORGANISM: Artificial Sequence
<220> FEATURE:
<223> OTHER INFORMATION: Description of Artificial Sequence: Synthetic
      light chain variable region

<400> SEQUENCE: 28

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg

<210> SEQ ID NO 29
<211> LENGTH: 448
<212> TYPE: PRT
<213> ORGANISM: Artificial Sequence
<220> FEATURE:
<223> OTHER INFORMATION: Description of Artificial Sequence: Synthetic
      heavy chain complete

<400> SEQUENCE: 29

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

```
Trp Ile Asn Trp Val Arg Gln Ala Pro Gly Gln Gly Leu Glu Trp Met
         35                  40                  45
Gly Arg Ile Phe Pro Gly Asp Gly Asp Thr Asp Tyr Asn Gly Lys Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asn Val Phe Asp Gly Tyr Trp Leu Val Tyr Trp Gly Gln Gly
                100                 105                 110
Thr Leu Val Thr Val Ser Ser Ala Ser Thr Lys Gly Pro Ser Val Phe
             115                 120                 125
Pro Leu Ala Pro Ser Ser Lys Ser Thr Ser Gly Gly Thr Ala Ala Leu
 130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
<210> SEQ ID NO 30
<211> LENGTH: 219
<212> TYPE: PRT
<213> ORGANISM: Artificial Sequence
<220> FEATURE:
<223> OTHER INFORMATION: Description of Artificial Sequence: Synthetic
      light chain complete

<400> SEQUENCE: 30

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 31

Gly Arg Thr Phe Thr Ser Tyr Asn Met His
1               5                   10

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 32

Ala Ile Tyr Pro Leu Thr Gly Asp Thr Ser Tyr Asn Gln Lys Ser Lys
```

-continued

```
<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 33

Ser Thr Tyr Val Gly Gly Asp Trp Gln Phe Asp Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 34

Arg Ala Ser Ser Ser Val Pro Tyr Ile His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 35

Ala Thr Ser Ala Leu Ala Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 36

Gln Gln Trp Leu Ser Asn Pro Pro Thr
1               5

<210> SEQ ID NO 37
<211> LENGTH: 121
<212> TYPE: PRT
<213> ORGANISM: Artificial Sequence
<220> FEATURE:
<223> OTHER INFORMATION: Description of Artificial Sequence: Synthetic
      heavy chain variable region

<400> SEQUENCE: 37

Glu Val Gln Leu Val Gln Ser Gly Ala Glu Val Lys Lys Pro Gly Glu
1               5                   10                  15

Ser Leu Lys Ile Ser Cys Lys Gly Ser Gly Arg Thr Phe Thr Ser Tyr
                20                  25                  30

Asn Met His Trp Val Arg Gln Met Pro Gly Lys Gly Leu Glu Trp Met
            35                  40                  45

Gly Ala Ile Tyr Pro Leu Thr Gly Asp Thr Ser Tyr Asn Gln Lys Ser
```

```
                    50                  55                  60
Lys Leu Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                     85                  90                  95

Ala Arg Ser Thr Tyr Val Gly Gly Asp Trp Gln Phe Asp Val Trp Gly
                    100                 105                 110

Lys Gly Thr Thr Val Thr Val Ser Ser
                    115                 120

<210> SEQ ID NO 38
<211> LENGTH: 106
<212> TYPE: PRT
<213> ORGANISM: Artificial Sequence
<220> FEATURE:
<223> OTHER INFORMATION: Description of Artificial Sequence: Synthetic
      light chain variable region

<400> SEQUENCE: 38

Glu Ile Val Leu Thr Gln Ser Pro Gly Thr Leu Ser Leu Ser Pro Gly
  1                   5                  10                  15

Glu Arg Ala Thr Leu Ser Cys Arg Ala Ser Ser Val Pro Tyr Ile
                     20                  25                  30

His Trp Tyr Gln Gln Lys Pro Gly Gln Ala Pro Arg Leu Leu Ile Tyr
                     35                  40                  45

Ala Thr Ser Ala Leu Ala Ser Gly Ile Pro Asp Arg Phe Ser Gly Ser
                     50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Leu Ser Asn Pro Pro Thr
                     85                  90                  95

Phe Gly Gln Gly Thr Lys Leu Glu Ile Lys
                    100                 105

<210> SEQ ID NO 39
<211> LENGTH: 451
<212> TYPE: PRT
<213> ORGANISM: Artificial Sequence
<220> FEATURE:
<223> OTHER INFORMATION: Description of Artificial Sequence: Synthetic
      heavy chain complete

<400> SEQUENCE: 39

Glu Val Gln Leu Val Gln Ser Gly Ala Glu Val Lys Lys Pro Gly Glu
  1                   5                  10                  15

Ser Leu Lys Ile Ser Cys Lys Gly Ser Gly Arg Thr Phe Thr Ser Tyr
                     20                  25                  30

Asn Met His Trp Val Arg Gln Met Pro Gly Lys Gly Leu Glu Trp Met
                     35                  40                  45

Gly Ala Ile Tyr Pro Leu Thr Gly Asp Thr Ser Tyr Asn Gln Lys Ser
 50                  55                  60

Lys Leu Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                     85                  90                  95

Ala Arg Ser Thr Tyr Val Gly Gly Asp Trp Gln Phe Asp Val Trp Gly
                    100                 105                 110

Lys Gly Thr Thr Val Thr Val Ser Ser Ala Ser Thr Lys Gly Pro Ser
```

```
            115                 120                 125
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 40
<211> LENGTH: 213
<212> TYPE: PRT
<213> ORGANISM: Artificial Sequence
<220> FEATURE:
<223> OTHER INFORMATION: Description of Artificial Sequence: Synthetic
      light chain complete

<400> SEQUENCE: 40

Glu Ile Val Leu Thr Gln Ser Pro Gly Thr Leu Ser Leu Ser Pro Gly
1               5                   10                  15
```

-continued

```
Glu Arg Ala Thr Leu Ser Cys Arg Ala Ser Ser Val Pro Tyr Ile
            20                  25                  30

His Trp Tyr Gln Gln Lys Pro Gly Gln Ala Pro Arg Leu Leu Ile Tyr
        35                  40                  45

Ala Thr Ser Ala Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Trp Leu Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 41

Gly Tyr Thr Phe Thr Ser Tyr Asn Met His
 1               5                  10

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain complementarity determining region
<220> FEATURE:
<221> NAME/KEY: MOD_RES
<222> LOCATION: (8)..(8)
<223> OTHER INFORMATION: Asp or Ala

<400> SEQUENCE: 42

Ala Ile Tyr Pro Gly Asn Gly Xaa Thr Ser Tyr Asn Gln Lys Phe Lys
 1               5                  10                  15

Gly

<210> SEQ ID NO 43
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      heavy chain complementarity determining region
<220> FEATURE:
<221> NAME/KEY: MOD_RES
<222> LOCATION: (6)..(6)
<223> OTHER INFORMATION: Asn, Ala, Tyr, Trp or Asp
<220> FEATURE:
<221> NAME/KEY: MOD_RES
<222> LOCATION: (7)..(7)
<223> OTHER INFORMATION: Ser or Arg

<400> SEQUENCE: 43

Val Val Tyr Tyr Ser Xaa Xaa Tyr Trp Tyr Phe Asp Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      light chain complementarity determining region
<220> FEATURE:
<221> NAME/KEY: MOD_RES
<222> LOCATION: (9)..(9)
<223> OTHER INFORMATION: Met or Leu

<400> SEQUENCE: 44

Arg Ala Ser Ser Ser Val Ser Tyr Xaa His
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 45

Ala Pro Ser Asn Leu Ala Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain complementarity determining region
<220> FEATURE:
<221> NAME/KEY: MOD_RES
<222> LOCATION: (4)..(4)
<223> OTHER INFORMATION: Ser or Ala

<400> SEQUENCE: 46

Gln Gln Trp Xaa Phe Asn Pro Pro Thr
1               5

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      heavy chain variable region

<400> SEQUENCE: 47

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
 50                  55                  60

Lys Gly Arg Phe Thr Ile Ser Val Asp Lys Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ser
            115                 120

<210> SEQ ID NO 48
<211> LENGTH: 107
<212> TYPE: PRT
<213> ORGANISM: Artificial Sequence
<220> FEATURE:
<223> OTHER INFORMATION: Description of Artificial Sequence: Synthetic
      light chain variable region

<400> SEQUENCE: 48

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
            35                  40                  45

Ala Pro Ser Asn Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg
            100                 105

<210> SEQ ID NO 49
<211> LENGTH: 452
<212> TYPE: PRT
<213> ORGANISM: Artificial Sequence
<220> FEATURE:
<223> OTHER INFORMATION: Description of Artificial Sequence: Synthetic
      heavy chain complete

<400> SEQUENCE: 49

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Thr Ser Tyr
            20                  25                  30

Asn Met His Trp Val Arg Gln Ala Pro Gly Lys Gly Leu Glu Trp Val
            35                  40                  45

Gly Ala Ile Tyr Pro Gly Asn Gly Asp Thr Ser Tyr Asn Gln Lys Phe
 50                  55                  60

Lys Gly Arg Phe Thr Ile Ser Val Asp Lys Ser Lys Asn Thr Leu Tyr
 65                  70                  75                  80
```

Leu Gln Met Asn Ser Leu Arg Ala Glu Asp Thr Ala Val Tyr Tyr Cys
                85                  90                  95

Ala Arg Val Val Tyr Tyr Ser Asn Ser Tyr Trp Tyr Phe Asp Val Trp
            100                 105                 110

Gly Gln Gly Thr Leu Val Thr Val Ser Ala Ser Thr Lys Gly Pro
            115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 50
<211> LENGTH: 213
<212> TYPE: PRT
<213> ORGANISM: Artificial Sequence
<220> FEATURE:

<223> OTHER INFORMATION: Description of Artificial Sequence: Synthetic
      light chain complete

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
                35                  40                  45

Ala Pro Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Phe Asn Pro Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 51

Ser Ser Val Ser Tyr Met His
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 52

Ala Pro Ser Asn Leu Ala Ser
1               5

<210> SEQ ID NO 53
<211> LENGTH: 499
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 53

Met Asp Phe Gln Val Gln Ile Phe Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Met His Trp Tyr Gln Gln Lys Pro Gly Ser Ser
    50                  55                  60

Pro Lys Pro Trp Ile Tyr Ala Pro Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Ser Phe Asn Pro Pro Thr Phe Gly Ala Gly Thr Lys Leu Glu Leu Lys
        115                 120                 125

Asp Gly Gly Gly Ser Gly Gly Gly Ser Gly Gly Gly Ser Ser
130                 135                 140

Gln Ala Tyr Leu Gln Gln Ser Gly Ala Glu Ser Val Arg Pro Gly Ala
145                 150                 155                 160

Ser Val Lys Met Ser Cys Lys Ala Ser Gly Tyr Thr Phe Thr Ser Tyr
                165                 170                 175

Asn Met His Trp Val Lys Gln Thr Pro Arg Gln Gly Leu Glu Trp Ile
            180                 185                 190

Gly Ala Ile Tyr Pro Gly Asn Gly Asp Thr Ser Tyr Asn Gln Lys Phe
        195                 200                 205

Lys Gly Lys Ala Thr Leu Thr Val Asp Lys Ser Ser Ser Thr Ala Tyr
    210                 215                 220

Met Gln Leu Ser Ser Leu Thr Ser Glu Asp Ser Ala Val Tyr Phe Cys
225                 230                 235                 240

Ala Arg Val Val Tyr Tyr Ser Asn Ser Tyr Trp Tyr Phe Asp Val Trp
                245                 250                 255

Gly Thr Gly Thr Thr Val Thr Val Ser Asp Gln Glu Pro Lys Ser Cys
            260                 265                 270

Asp Lys Thr His Thr Ser Pro Pro Cys Ser Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

```
Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 54

Ser Tyr Asn Met His
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 55

Ala Ile Tyr Pro Gly Asn Gly Asp Thr Ser Tyr Asn Gln Lys Phe Lys
1               5                   10                  15

Gly

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 56

Ser Thr Tyr Tyr Gly Gly Asp Trp Tyr Phe Asp Val
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 57

Arg Ala Ser Ser Ser Val Ser Tyr Ile His
```

<210> SEQ ID NO 58
<211> LENGTH: 120
<212> TYPE: PRT
<213> ORGANISM: Artificial Sequence
<220> FEATURE:
<223> OTHER INFORMATION: Description of Artificial Sequence: Synthetic heavy chain variable region

<400> SEQUENCE: 58

```
Gln Val Gln Leu Gln Gln Ser Gly Ala Glu Val Lys Pro Gly Ser
1               5                   10                  15

Ser Val Lys Val Ser Cys Lys Ala Ser Gly Tyr Thr Phe Thr Ser Tyr
                20                  25                  30

Asn Met His Trp Val Lys Gln Ala Pro Gly Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
                100                 105                 110

Gln Gly Thr Thr Val Thr Val Ser
            115                 120
```

<210> SEQ ID NO 59
<211> LENGTH: 106
<212> TYPE: PRT
<213> ORGANISM: Artificial Sequence
<220> FEATURE:
<223> OTHER INFORMATION: Description of Artificial Sequence: Synthetic light chain variable region

<400> SEQUENCE: 59

```
Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Ser Val Ser Tyr Ile
                20                  25                  30

His Trp Phe Gln Gln Lys Pro Gly Lys Ala Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Thr Ser Asn Pro Pro Thr
                85                  90                  95

Phe Gly Gly Gly Thr Lys Leu Glu Ile Lys
                100                 105
```

<210> SEQ ID NO 60
<211> LENGTH: 451
<212> TYPE: PRT
<213> ORGANISM: Artificial Sequence
<220> FEATURE:
<223> OTHER INFORMATION: Description of Artificial Sequence: Synthetic heavy chain complete

<400> SEQUENCE: 60

```
Gln Val Gln Leu Gln Gln Ser Gly Ala Glu Lys Lys Pro Gly Ser
1               5                   10                  15

Ser Val Lys Val Ser Cys Lys Ala Ser Gly Tyr Thr Phe Thr Ser Tyr
            20                  25                  30

Asn Met His Trp Val Lys Gln Ala Pro Gly Gln Gly Leu Glu Trp Ile
                35                  40                  45

Gly Ala Ile Tyr Pro Gly Met Gly Asp Thr Ser Tyr Asn Gln Lys Phe
            50                  55                  60

Lys Gly Lys Ala Thr Leu Thr Ala Asp Glu Ser Thr Asn Thr Ala Tyr
65                  70                  75                  80

Met Glu Leu Ser Ser Leu Arg Ser Glu Asp Thr Ala Phe Tyr Tyr Cys
                85                  90                  95

Ala Arg Ser Thr Tyr Tyr Gly Gly Asp Trp Tyr Phe Asp Val Trp Gly
                100                 105                 110

Gln Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 61
<211> LENGTH: 213
<212> TYPE: PRT
<213> ORGANISM: Artificial Sequence
<220> FEATURE:
<223> OTHER INFORMATION: Description of Artificial Sequence: Synthetic
      light chain complete

<400> SEQUENCE: 61

Asp Ile Gln Leu Thr Gln Ser Pro Ser Ser Leu Ser Ala Ser Val Gly
1               5                   10                  15

Asp Arg Val Thr Met Thr Cys Arg Ala Ser Ser Ser Val Ser Tyr Ile
            20                  25                  30

His Trp Phe Gln Gln Lys Pro Gly Lys Ala Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 62
<211> LENGTH: 122
<212> TYPE: PRT
<213> ORGANISM: Artificial Sequence
<220> FEATURE:
<223> OTHER INFORMATION: Description of Artificial Sequence: Synthetic
      heavy chain variable region

<400> SEQUENCE: 62

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

```
Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala
        115                 120

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      heavy chain complementarity determining region

<400> SEQUENCE: 63

Ala Arg Tyr Asp Tyr Asn Tyr Ala Met Asp Tyr
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      light chain complementarity determining region

<400> SEQUENCE: 64

Gln Gln Trp Thr Phe Asn Pro Pro Thr
1               5

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      heavy chain variable region

<400> SEQUENCE: 65

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Asn Met His Trp Val Lys Gln Thr Pro Arg Gln Gly Leu Glu Trp Ile
            35                  40                  45

Gly Gly Ile Tyr Pro Gly Asn Gly Asp Thr Ser Tyr Asn Gln Lys Phe
        50                  55                  60

Lys Gly Lys Ala Thr Leu Thr Val Gly Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Tyr Asp Tyr Asn Tyr Ala Met Asp Tyr Trp Gly Gln Gly Thr
            100                 105                 110

Ser Val Thr Val Ser Ser
```

<210> SEQ ID NO 66
<211> LENGTH: 106
<212> TYPE: PRT
<213> ORGANISM: Artificial Sequence
<220> FEATURE:
<223> OTHER INFORMATION: Description of Artificial Sequence: Synthetic
      light chain variable region

<400> SEQUENCE: 66

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Phe Thr Ile Ser Arg Val Glu Ala Glu
65                  70                  75                  80

Asp Ala Ala Thr Tyr Tyr Cys Gln Gln Trp Thr Phe Asn Pro Pro Thr
                85                  90                  95

Phe Gly Gly Gly Thr Arg Leu Glu Ile Lys
            100                 105

<210> SEQ ID NO 67
<211> LENGTH: 330
<212> TYPE: PRT
<213> ORGANISM: Artificial Sequence
<220> FEATURE:
<223> OTHER INFORMATION: Description of Artificial Sequence: Synthetic
      heavy chain complete

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 68
<211> LENGTH: 106
<212> TYPE: PRT
<213> ORGANISM: Artificial Sequence
<220> FEATURE:
<223> OTHER INFORMATION: Description of Artificial Sequence: Synthetic
      light chain complete

<400> SEQUENCE: 68

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

METHODS OF USE AND PHARMACEUTICAL COMBINATIONS OF HISTONE DEACETYLASE INHIBITORS AND CD20 INHIBITORY ANTIBODIES

CROSS-REFERENCE TO RELATED APPLICATIONS

This application claims the benefit of U.S. Provisional Application No. 62/372,093, filed Aug. 8, 2016, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 28, 2017, is named 593474 ACT-045_SL.txt and is 70,787 bytes in size.

BACKGROUND

Histone deacetylase (HDAC) inhibition can cause cancer cell growth arrest. However, pan-HDAC inhibition leads to significant adverse effects, and an alternative HDAC inhibition profile is desirable.

HDAC6 is a Class IIb HDAC and is known to remove acetyl groups from many cellular proteins, including α-tubulin and HSP90. It has been reported that HSP90 hyperacetylation destabilizes its target proteins, including ER and EGFR. Inhibitors of HDAC6 have demonstrated anti-cancer proliferative activity in various cancer types. Blocking HDAC6 activity has been shown to cause cancer cell growth inhibition through various mechanisms.

B-lymphocyte antigen CD20 (CD20) is a glycosylated phosphoprotein expressed on the surface of all B-cells. CD20 enables a B-cell immune response against antigens. CD20 is targeted by CD20 inhibitory antibodies. CD20 inhibitory antibodies can treat a B-cell disorder, including cancer, an autoimmune disorder, or a transplant rejection.

Due to the dose-limiting toxicities of current pan-selective HDAC inhibitors, there is an ongoing need for improved methods for the treatment of cancer.

SUMMARY

In order to provide alternative efficacious and less toxic cancer treatments, provided herein are methods for the treatment of a B-cell disorder (e.g., cancer), and pharmaceutical combinations comprising an HDAC inhibitor and a CD20 inhibitory antibody. The pharmaceutical combinations and methods disclosed herein are well tolerated and do not exhibit the dose-limiting toxicities of prior therapies.

In one aspect, provided herein are methods for treating a B-cell disorder, such as cancer, an autoimmune disorder, or a transplant rejection, in a subject in need thereof. In particular, provided herein are methods for treating a B-cell disorder in a subject in need thereof comprising administering to the subject a therapeutically effective amount of an HDAC6 selective inhibitor and a therapeutically effective amount of a CD20 inhibitory antibody. In another embodiment, provided herein are methods for treating a B-cell disorder in a subject in need thereof, comprising administering to the subject a therapeutically effective amount of:

a) an HDAC6 selective inhibitor, wherein the HDAC6 selective inhibitor is Compound A

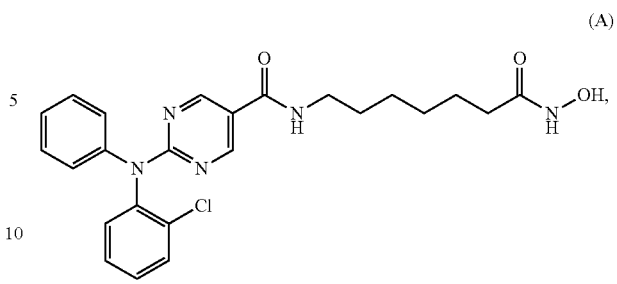

(A)

or a pharmaceutically acceptable salt thereof; and
b) a CD20 inhibitory antibody.

In another embodiment, provided herein are methods for treating a B-cell disorder in a subject in need thereof, comprising administering to the subject a therapeutically effective amount of:

a) an HDAC6 selective inhibitor, wherein the HDAC6 selective inhibitor is Compound B

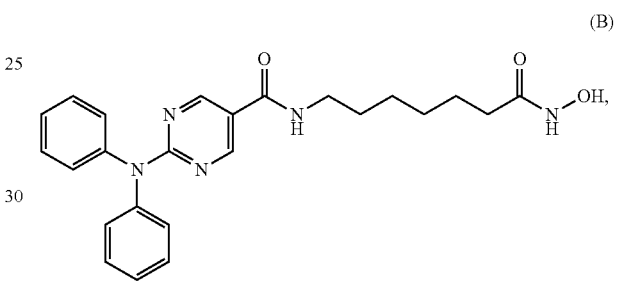

(B)

or a pharmaceutically acceptable salt thereof; and
b) a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In another embodiment, provided herein are methods for treating a B-cell disorder in a subject in need thereof, comprising administering to the subject a therapeutically effective amount of:

a) an HDAC6 selective inhibitor, wherein the HDAC6 selective inhibitor is a compound of Formula I

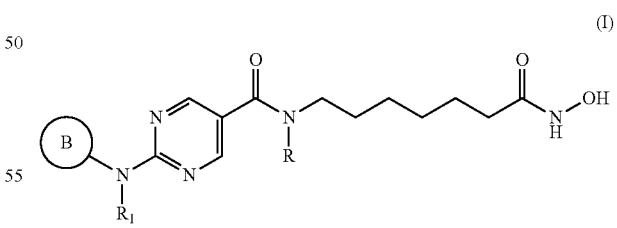

(I)

or a pharmaceutically acceptable salt thereof,
wherein
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl; and
b) a CD20 inhibitory antibody. In an embodiment, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In an embodiment of Formula I, $R_1$ is an aryl that is substituted by OH, halo, or $C_{1-6}$-alkyl.

In some embodiments of the methods disclosed herein, the B-cell disorder is an autoimmune disorder or transplant rejection.

In other embodiments of the methods disclosed herein, the autoimmune disorder is selected from anti-N-methyl D-aspartate (NMDA) receptor encephalitis, autoimmune anemia, autoimmune pancreatitis, bullous skin disorders, chronic inflammatory demyelinating polyneuropathy, Evans syndrome, Graves' ophthalmopathy, idiopathic thrombocytopenic purpura (ITP), IgG4-related disease, pure red cell aplasia, multiple sclerosis, neuromyelitis optica (Devic's disease), opsoclonus myoclonus syndrome (OMS), rheumatoid arthritis, Sjogren's syndrome, systemic lupus erythematosus, thrombotic thrombocytopenic purpura (TTP), type 1 diabetes mellitus, and vasculitis. In another embodiment of the methods disclosed herein, the vasculitis is granulomatosis with polyangiitis (GPA) (Wegner's granulomatosis) or microscopic polyangiitis (MPA).

In some embodiments of the methods disclosed herein, the B-cell disorder is cancer. In other embodiments, provided herein are methods for treating cancer in a subject in need thereof, comprising administering to the subject a therapeutically effective amount of:

a) an HDAC6 selective inhibitor, wherein the HDAC6 selective inhibitor is Compound A

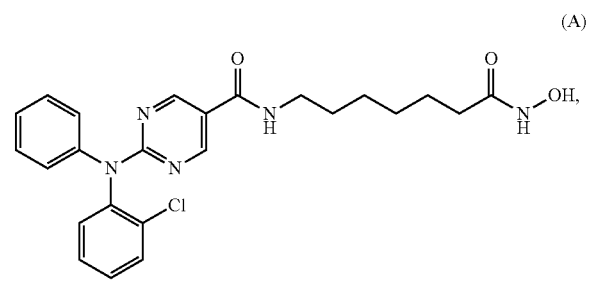 [SMILES: O=C(CCCCCCNC(=O)c1cnc(N(c2ccccc2)c2ccccc2Cl)nc1)NO]

(A)

or a pharmaceutically acceptable salt thereof; and b) a CD20 inhibitory antibody.

In other embodiments, provided herein are methods for treating cancer in a subject in need thereof, comprising administering to the subject a therapeutically effective amount of:

a) an HDAC6 selective inhibitor, wherein the HDAC6 selective inhibitor is Compound B

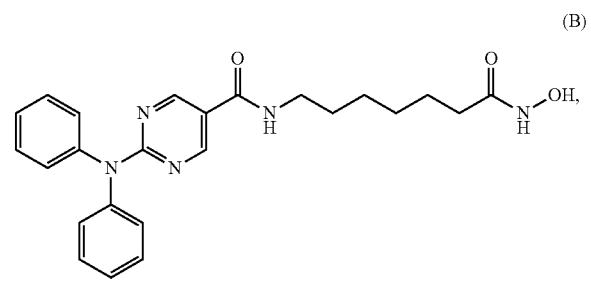 [SMILES: O=C(CCCCCCNC(=O)c1cnc(N(c2ccccc2)c2ccccc2)nc1)NO]

(B)

or a pharmaceutically acceptable salt thereof; and b) a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In another embodiment, provided herein are methods for treating cancer in a subject in need thereof, comprising administering to the subject a therapeutically effective amount of:

a) an HDAC6 selective inhibitor, wherein the HDAC6 selective inhibitor is a compound of Formula I

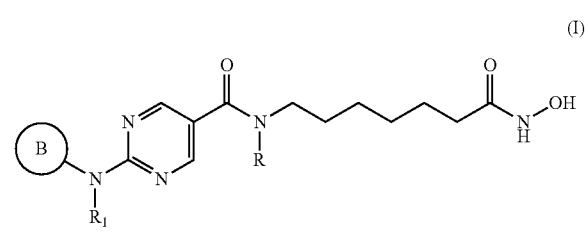

(I)

or a pharmaceutically acceptable salt thereof, wherein ring B is aryl or heteroaryl;

$R_1$ is an aryl or heteroaryl, each of which may be optionally substituted by OH, halo, or $C_{1-6}$-alkyl;

and

R is H or $C_{1-6}$-alkyl; and b) a CD20 inhibitory antibody. In an embodiment, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In an embodiment of Formula I, $R_1$ is an aryl that is substituted by OH, halo, or $C_{1-6}$-alkyl.

In another embodiment of the methods provided herein, the cancer is a hematologic malignancy. In yet another embodiment, the cancer is a leukemia, a lymphoma, or a myeloma. In still another embodiment, the cancer is selected from the group consisting of acute lymphoblastic leukemia, B-cell leukemia, chronic lymphocytic leukemia, acute myeloid leukemia, chronic myeloid leukemia, B-cell lymphoma, Burkitt lymphoma, diffuse large B-cell lymphoma, non-Hodgkin's lymphoma, lymphocyte predominant subtype of Hodgkin's lymphoma, mantle cell lymphoma, and multiple myeloma. In a further embodiment, the cancer is selected from the group consisting of chronic lymphocytic leukemia, non-Hodgkin's lymphoma, and multiple myeloma. In another embodiment, the cancer is multiple myeloma.

In other aspects, provided herein are methods for upregulating antibody-dependent cell-mediated cytotoxicity in a subject in need thereof, comprising administering to the subject a therapeutically effective amount of:

a) an HDAC6 selective inhibitor, wherein the HDAC6 selective inhibitor is Compound A

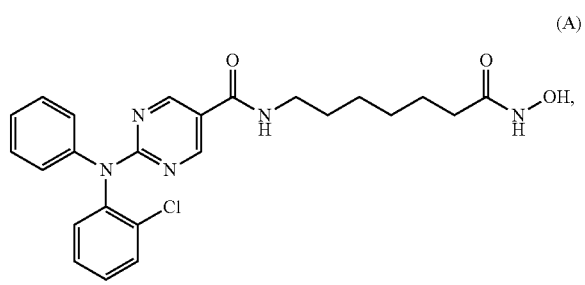 [SMILES: O=C(CCCCCCNC(=O)c1cnc(N(c2ccccc2)c2ccccc2Cl)nc1)NO]

(A)

or a pharmaceutically acceptable salt thereof; and b) a CD20 inhibitory antibody.

In another aspect, provided herein are methods for upregulating antibody-dependent cell-mediated cytotoxicity in a subject in need thereof, comprising administering to the subject a therapeutically effective amount of:

a) an HDAC6 selective inhibitor, wherein the HDAC6 selective inhibitor is Compound B

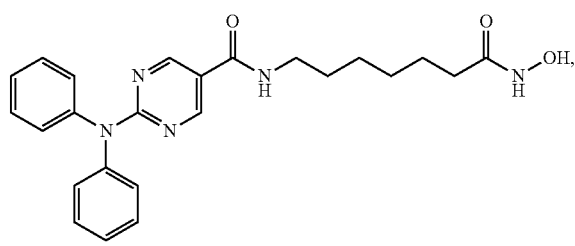

(B)

or a pharmaceutically acceptable salt thereof; and b) a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In another embodiment, provided herein are methods for upregulating antibody-dependent cell-mediated cytotoxicity in a subject in need thereof, comprising administering to the subject a therapeutically effective amount of:

a) an HDAC6 selective inhibitor, wherein the HDAC6 selective inhibitor is a compound of Formula I

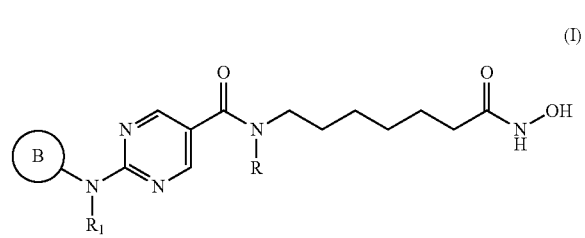

(I)

or a pharmaceutically acceptable salt thereof, wherein ring B is aryl or heteroaryl;

$R_1$ is an aryl or heteroaryl, each of which may be optionally substituted by OH, halo, or $C_{1-6}$-alkyl;

and

R is H or $C_{1-6}$-alkyl; and b) a CD20 inhibitory antibody. In an embodiment, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In an embodiment of Formula I, $R_1$ is an aryl that is substituted by OH, halo, or $C_{1-6}$-alkyl.

In yet another aspect, provided herein are methods for upregulating lymphocyte functional activity in a subject in need thereof, comprising administering to the subject a therapeutically effective amount of:

a) an HDAC6 selective inhibitor, wherein the HDAC6 selective inhibitor is Compound A

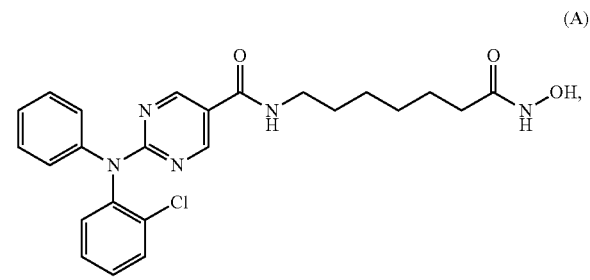 [SMILES: O=C(CCCCCCNC(=O)c1cnc(N(c2ccccc2)c2ccccc2Cl)nc1)NO]

(A)

or a pharmaceutically acceptable salt thereof; and b) a CD20 inhibitory antibody.

In still another aspect, provided herein are methods for upregulating lymphocyte functional activity in a subject in need thereof, comprising administering to the subject a therapeutically effective amount of:

a) an HDAC6 selective inhibitor, wherein the HDAC6 selective inhibitor is Compound B

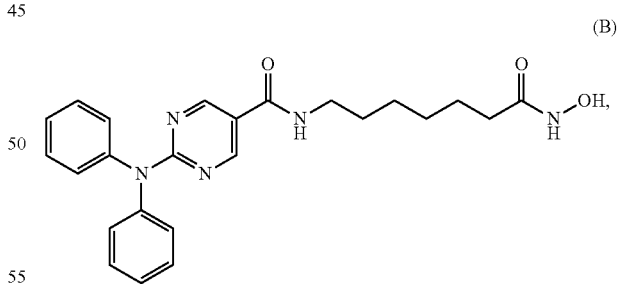

(B)

or a pharmaceutically acceptable salt thereof; and b) a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In another embodiment, provided herein are methods for upregulating lymphocyte functional activity in a subject in need thereof, comprising administering to the subject a therapeutically effective amount of:

a) an HDAC6 selective inhibitor, wherein the HDAC6 selective inhibitor is a compound of Formula I

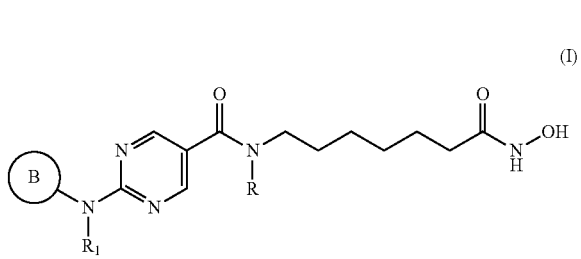

or a pharmaceutically acceptable salt thereof,
wherein
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl; and
b) a CD20 inhibitory antibody. In an embodiment, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In an embodiment of Formula I, $R_1$ is an aryl that is substituted by OH, halo, or $C_{1-6}$-alkyl.

In some embodiments of the methods disclosed herein, the lymphocyte is a natural killer cell. In other embodiments, the lymphocyte is a T lymphocyte. In another embodiment, the lymphocyte is a B lymphocyte. In yet another embodiment, the B lymphocyte is a follicular B lymphocyte. In still another embodiment, the B lymphocyte is a diffuse large B-cell.

In other embodiments of the methods disclosed herein, the expression of CD20 on a cancer cell is upregulated. In some embodiments of the methods disclosed herein, the expression of CD20 on a chronic lymphocytic leukemia cell is upregulated. In another embodiment of the methods disclosed herein, the expression of CD20 on a non-Hodgkin's lymphoma cell is upregulated. In still another embodiment of the methods disclosed herein, the expression of CD20 on a multiple myeloma cell is upregulated.

In yet another aspect, provided herein are methods of upregulating the expression of CD20 in a cell comprising contacting the cell with an HDAC6 selective inhibitor, wherein the HDAC6 selective inhibitor is Compound A

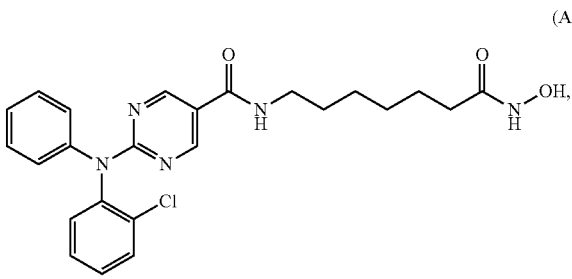

or a pharmaceutically acceptable salt thereof.

In still another aspect, provided herein are methods of upregulating the expression of CD20 in a cell comprising contacting the cell with an HDAC6 selective inhibitor, wherein the HDAC6 selective inhibitor is Compound B

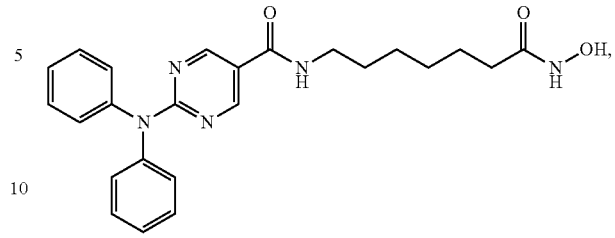

or a pharmaceutically acceptable salt thereof.

In another embodiment, provided herein are methods for upregulating the expression of CD20 in a cell comprising contacting the cell with an HDAC6 selective inhibitor, wherein the HDAC6 selective inhibitor is a compound of Formula I

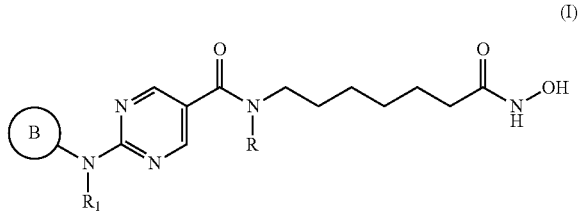

or a pharmaceutically acceptable salt thereof,
wherein
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl. In an embodiment, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In an embodiment of Formula I, $R_1$ is an aryl that is substituted by OH, halo, or $C_{1-6}$-alkyl.

In some embodiments of the methods disclosed herein, the cell is a cancer cell. In another embodiment, the cell is a chronic lymphocytic leukemia cell. In still another embodiment, the cell is a non-Hodgkin's lymphoma cell. In yet another embodiment, the cell is a multiple myeloma cell.

In other embodiments of the methods disclosed herein, the viability of a peripheral blood mononuclear cell is maintained. In another embodiment, the peripheral blood mononuclear cell is a CD20+ B lymphocyte, a CD20+ follicular B lymphocyte, or a CD20+ diffuse large B-cell.

In some embodiments of the methods and the pharmaceutical combinations disclosed herein, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

In other embodiments of the methods and the pharmaceutical combinations disclosed herein, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In one embodiment of the methods and the pharmaceutical combinations disclosed herein, the CD20 inhibitory antibody comprises three heavy chain complementarity determining regions (CDRs) set forth in SEQ ID NOs: 1-3 and three light chain CDRs set forth in SEQ ID NOs: 4-6. In another embodiment, the CD20 inhibitory antibody comprises a heavy chain variable region set forth in SEQ ID NO: 7, and a light chain variable region set forth in SEQ ID NO: 8. In yet another embodiment, the CD20 inhibitory antibody comprises a heavy chain variable region set forth in SEQ ID NO: 62, and a light chain variable region set forth in SEQ ID NO: 8. In still another embodiment, the CD20 inhibitory antibody comprises a heavy chain set forth in SEQ ID NO: 9, and a light chain set forth in SEQ ID NO: 10.

In yet another embodiment of the methods and the pharmaceutical combinations disclosed herein, the CD20 inhibitory antibody comprises three heavy chain CDRs set forth in SEQ ID NOs: 11-13 and three light chain CDRs set forth in SEQ ID NOs: 14-16. In some embodiments, the CD20 inhibitory antibody comprises a heavy chain variable region set forth in SEQ ID NO: 17, and a light chain variable region set forth in SEQ ID NO: 18. In another embodiment, the CD20 inhibitory antibody comprises a heavy chain set forth in SEQ ID NO: 19, and a light chain set forth in SEQ ID NO: 20.

In still another embodiment of the methods and the pharmaceutical combinations disclosed herein, the CD20 inhibitory antibody comprises three heavy chain CDRs set forth in SEQ ID NOs: 21-23 and three light chain CDRs set forth in SEQ ID NOs: 24-26. In another embodiment, the CD20 inhibitory antibody comprises a heavy chain variable region set forth in SEQ ID NO: 27, and a light chain variable region set forth in SEQ ID NO: 28. In some embodiments, the CD20 inhibitory antibody comprises a heavy chain set forth in SEQ ID NO: 29, and a light chain set forth in SEQ ID NO: 30.

In some embodiments of the methods disclosed herein, the HDAC6 selective inhibitor and the CD20 inhibitory antibody are administered at different times. In another embodiment, the HDAC6 selective inhibitor is administered orally, and the CD20 inhibitory antibody is administered intravenously.

In other embodiments of the methods disclosed herein, the cancer is resistant or refractory to treatment with the CD20 inhibitory antibody. In another embodiment of the methods disclosed herein, the chronic lymphocytic leukemia is resistant or refractory to treatment with the CD20 inhibitory antibody. In still another embodiment of the methods disclosed herein, the non-Hodgkin's lymphoma is resistant or refractory to treatment with the CD20 inhibitory antibody. In yet another embodiment of the methods disclosed herein, the multiple myeloma is resistant or refractory to treatment with the CD20 inhibitory antibody. In further embodiments of the methods disclosed herein, the cancer is resistant or refractory to treatment with a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

In another aspect, provided herein are pharmaceutical combinations, wherein the combination comprises a therapeutically effective amount of:

a) an HDAC6 selective inhibitor, wherein the HDAC6 selective inhibitor is Compound A

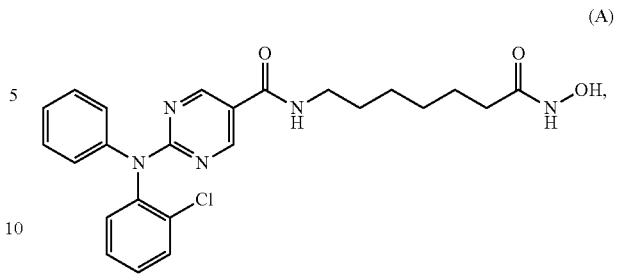

or a pharmaceutically acceptable salt thereof; and b) a CD20 inhibitory antibody.

In still another aspect, provided herein are pharmaceutical combinations, wherein the combination comprises a therapeutically effective amount of:

a) an HDAC6 selective inhibitor, wherein the HDAC6 selective inhibitor is Compound B

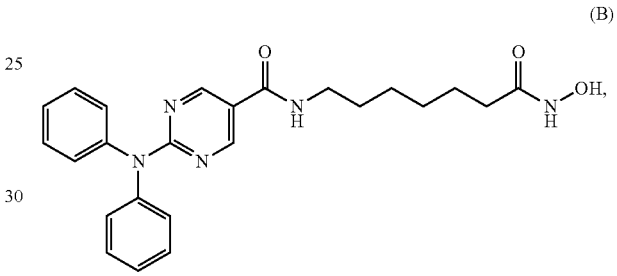

or a pharmaceutically acceptable salt thereof; and b) a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In another embodiment, provided herein are pharmaceutical combinations, wherein the combination comprises a therapeutically effective amount of:

a) an HDAC6 selective inhibitor, wherein the HDAC6 selective inhibitor is a compound of Formula I

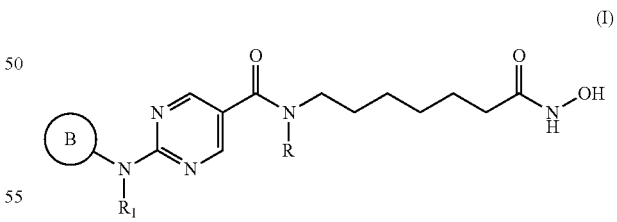

or a pharmaceutically acceptable salt thereof,
wherein
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl; and b) a CD20 inhibitory antibody. In an embodiment, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In an embodiment of Formula I, $R_1$ is an aryl that is substituted by OH, halo, or $C_{1-6}$-alkyl.

In some embodiments of the pharmaceutical combinations disclosed herein, the combination further comprises one or more pharmaceutically acceptable carriers.

Also provided herein are uses of the pharmaceutical combinations disclosed herein for the manufacture of a pharmaceutical preparation or medicament for the treatment of cancer.

Other objects, features, and advantages will become apparent from the following detailed description. The detailed description and specific examples are given for illustration only because various changes and modifications within the spirit and scope of the disclosure will become apparent to those skilled in the art from this detailed description. Further, the examples demonstrate the principle of the disclosure.

DETAILED DESCRIPTION

Figure 1A:
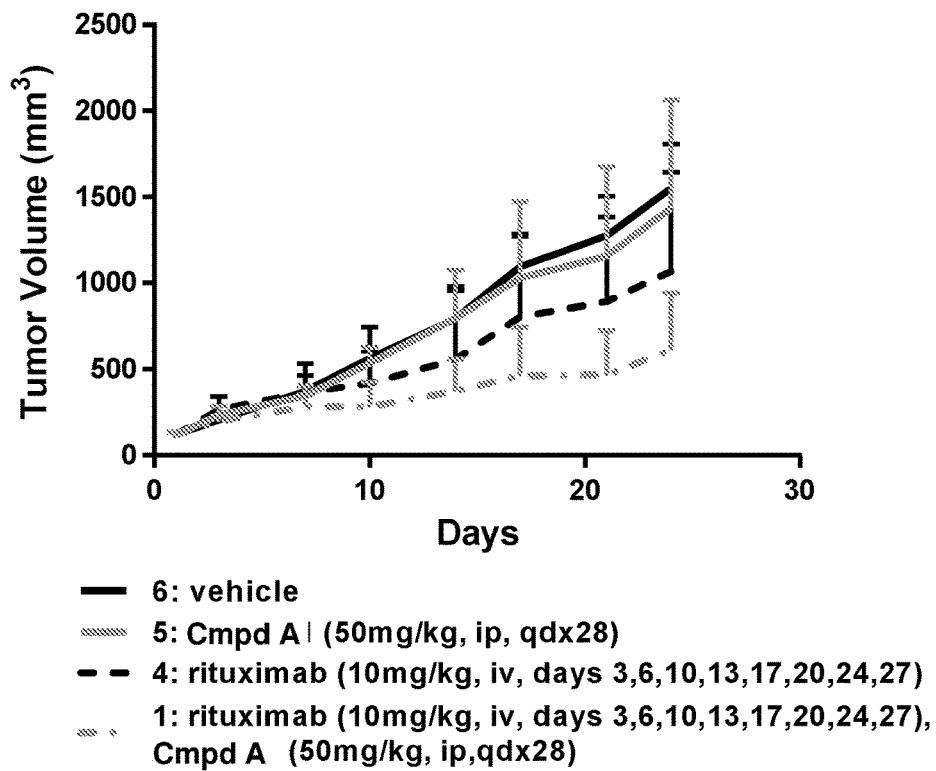
FIG. 1A shows tumor growth kinetics after treatment with the indicated drugs and antibodies.

The present disclosure is directed to methods of using a histone deacetylase (HDAC) inhibitor and a CD20 inhibitory antibody for the treatment of a B-cell disorder. Provided herein are methods for treating a B-cell disorder in a patient in need thereof comprising administering an HDAC inhibitor (e.g., a compound of Formula I) and a CD20 inhibitory antibody. Also provided herein are combination products and pharmaceutical combinations comprising an HDAC inhibitor (e.g., a compound of Formula I) and a CD20 inhibitory antibody.

Definitions

Listed below are definitions of various terms used in this disclosure. These definitions apply to the terms as they are used throughout this specification and claims, unless otherwise limited in specific instances, either individually or as part of a larger group.

As used in the specification and in the claims, the term "comprising" may include the embodiments "consisting of" and "consisting essentially of." The terms "comprise(s)," "include(s)," "having," "has," "may," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically acceptable carriers, and excludes other compounds.

The term "about" generally indicates a possible variation of no more than 10%, 5%, or 1% of a value. For example, "about 25 mg/kg" will generally indicate, in its broadest sense, a value of 22.5-27.5 mg/kg, i.e., 25±2.5 mg/kg.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "aryl" refers to a mono- or poly-cyclic carbocyclic ring system having one or more aromatic rings, fused or non-fused, including, but not limited to, phenyl, naphthyl, tetrahydronaphthyl, indanyl, idenyl, and the like.

The term "heteroaryl" refers to a mono- or poly-cyclic (e.g., bi-, or tri-cyclic or more) fused or non-fused, moieties or ring system having at least one aromatic ring, having from five to ten ring atoms of which one ring atom is selected from S, O, and N; zero, one or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "halo" refers to a halogen, such as fluorine, chlorine, bromine, and iodine.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

The term "HDAC6 selective" means that the compound binds to HDAC6 to a substantially greater extent, such as 5×, 10×, 15×, 20× greater or more, than to any other type of HDAC enzyme, such as HDAC1 or HDAC2. That is, the compound is selective for HDAC6 over any other type of HDAC enzyme. For example, a compound that binds to HDAC6 with an $IC_{50}$ of 10 nM and to HDAC1 with an $IC_{50}$ of 50 nM is HDAC6 selective. On the other hand, a compound that binds to HDAC6 with an $IC_{50}$ of 50 nM and to HDAC1 with an $IC_{50}$ of 60 nM is not HDAC6 selective.

The term "inhibitor" is synonymous with the term antagonist.

A "CD20 inhibitory antibody" targets B-lymphocyte antigen CD20 (CD20). The CD20 inhibitory antibody comprises three heavy chain complementarity determining regions (CDRs) and three light chain CDRs that bind to CD20. The CD20 inhibitory antibody can comprise a heavy chain variable region and a light chain variable region, which include the respective CDRs. The CD20 inhibitory antibody can comprise a heavy chain and a light chain, which include the respective variable regions. For example, a CD20 inhibitory antibody includes, but is not limited to, obinutuzumab, ocaratuzumab, ocrelizumab, ofatumumab, rituximab, TRU-015, and veltuzumab.

As used herein, the term "treatment" or "treating" indicates that the method has, at the least, mitigated the B-cell disorder. A method for treating comprises applying or administering to the subject a pharmaceutical combination comprising an HDAC6 selective inhibitor and a CD20 inhibitory antibody. A method for treating comprises applying or administering to an isolated tissue or cell line from a subject (e.g., for diagnosis or ex vivo applications), who has a B-cell disorder (e.g., cancer, an autoimmune disorder, transplant rejection) a pharmaceutical combination comprising an HDAC6 selective inhibitor and a CD20 inhibitory antibody. The purpose of application or administration of the pharmaceutical combination is to treat, cure, heal, alleviate, relieve, alter, remedy, ameliorate, improve or affect B-cell disorder. Such treatments may be specifically tailored or modified, based on knowledge obtained from the field of pharmacogenomics. The methods of the disclosure can, at the least, mitigate abnormal cellular proliferation. For example, the method can reduce the rate of cancer growth in a patient, or prevent the continued growth or spread of the cancer, or even reduce the overall reach of the cancer.

As used herein, the term "patient," "individual," or "subject" refers to a human or a non-human mammal. Non-human mammals include, for example, livestock and pets, such as ovine, bovine, porcine, canine, feline and murine mammals. Preferably, the patient, subject or individual is human.

As used herein, the term "autoimmune disorder" occurs when the body's immune system attacks and destroys healthy cells in the body by mistake. An autoimmune disorder includes, for example, anti-N-methyl D-aspartate (NMDA) receptor encephalitis, autoimmune anemia, autoimmune pancreatitis, bullous skin disorders, chronic inflammatory demyelinating polyneuropathy, Evans syndrome, Graves' ophthalmopathy, idiopathic thrombocytopenic purpura (ITP), IgG4-related disease, pure red cell aplasia, multiple sclerosis, neuromyelitis optica (Devic's disease), opsoclonus myoclonus syndrome (OMS), rheumatoid arthritis, Sjogren's syndrome, systemic lupus erythematosus, thrombotic thrombocytopenic purpura (TTP), type 1 diabetes mellitus, and vasculitis. In yet another embodiment, the vasculitis is granulomatosis with polyangiitis (GPA) (Wegner's granulomatosis) or microscopic polyangiitis (MPA).

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure may be synthesized from the parent compound which contains a basic or acidic moiety by conventional chemical methods. Generally, such salts may be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient.

The term "combination," "therapeutic combination," "pharmaceutical combination," or "combination product" as used herein refer to either a fixed combination in one dosage unit form, or a non-fixed combination in separate dosage units, or a kit of parts for the combined administration where two or more therapeutic agents may be administered independently, at the same time, at substantially different times, or separately within time intervals, especially where these time intervals allow that the combination partners show a cooperative, e.g., synergistic, effect.

The term "combination therapy" refers to the administration of two or more therapeutic agents to treat a therapeutic condition or disorder described in the present disclosure.

Such administration encompasses co-administration of these therapeutic agents in a substantially simultaneous manner, such as in a single formulation having a fixed ratio of active ingredients or in separate formulations (e.g., capsules and/or intravenous formulations) for each active ingredient. In addition, such administration also encompasses use of each type of therapeutic agent in a sequential or separate manner, either at approximately the same time or at different times. Such administration also encompasses each component being formulated as a separate formulation that can be administered at different times. For example, the CD20 inhibitory antibody rituximab can be dosed every week, every 21 days, every 28 days, or every two months while the HDAC inhibitor of Formula I can, for example, be dosed daily. In any case, the treatment regimen of the drug combination will provide beneficial effects in treating the conditions or disorders described herein.

The term "sub-therapeutically effective amount" or "sub-therapeutic dose" is an amount or dose of the active ingredient (e.g., an HDAC6 selective inhibitor or a CD20 inhibitory antibody), that, when administered to a patient by itself, does not completely inhibit over time the biological activity of the intended target.

The term "synergistic effect" refers to the action of two agents, such as, for example, an HDAC6 selective inhibitor and a CD20 inhibitory antibody, producing an effect, for example, slowing the symptomatic progression of a B-cell disorder, such as, for example, cancer, an autoimmune disorder, or transplant rejection, or symptoms thereof, which is greater than the simple addition of the effects of each drug administered alone. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984) and Chou, Pharmacol. Rev. 58: 621-681 (2006). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively. In some embodiments, the combinations described herein exhibit a synergistic effect (i.e., greater than additive effect) in the treatment of cancer. In further embodiments, the combinations described herein exhibit a synergistic effect (i.e., greater than additive effect) in the treatment of B-Cell disorders.

As used herein, the term "resistant" or "refractive" to a therapeutic agent when referring to a B-cell disorder (e.g., cancer) patient means that the B-cell disorder (e.g., cancer) has innate, or achieved resistance to, the effects of the therapeutic agent as a result of contact with the therapeutic agent. Stated alternatively, the B-cell disorder patient is resistant to the ordinary standard of care associated with the particular therapeutic agent.

As used herein, "treatment naïve" refers to the patient not having previously received treatment with a drug, either investigational or approved, for a B-cell disorder, such as cancer, in particular, a CD20 inhibitory antibody.

Alternatively, patients treated according to the methods of the disclosure may be "treatment experienced." As used herein, "treatment experienced" refers to a patient who has had at least one previous course of a B-cell disorder therapy, in particular a CD20 inhibitory antibody. In some embodiments, the last dose in this previous course occurred at least three months prior to implementing a method according to the present disclosure.

Histone Deacetylase (HDAC) Inhibitors

Provided herein are methods for treating a B-cell disorder in a subject in need thereof, comprising administering an HDAC inhibitor and a CD20 inhibitory antibody. Also provided herein are pharmaceutical combinations comprising an HDAC inhibitor and a CD20 inhibitory antibody.

The pharmaceutical combinations and methods disclosed herein comprise a histone deacetylase (HDAC) inhibitor. The HDAC inhibitor may be any HDAC inhibitor. Thus, the HDAC inhibitor may be selective or non-selective to a particular type of histone deacetylase enzyme. Preferably, the HDAC inhibitor is a selective HDAC inhibitor. More preferably, the HDAC inhibitor is an HDAC6 selective inhibitor.

In some embodiments, the HDAC6 selective inhibitor is a compound of Formula I:

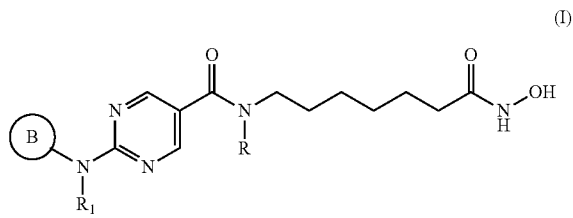

(I)

or a pharmaceutically acceptable salt thereof, wherein ring B is aryl or heteroaryl;

$R_1$ is an aryl or heteroaryl, each of which may be optionally substituted by OH, halo, or $C_{1-6}$-alkyl;

and

R is H or $C_{1-6}$-alkyl.

In an embodiment of Formula I, $R_1$ is an aryl that is substituted by OH, halo, or $C_{1-6}$-alkyl.

Representative compounds of Formula I include, but are not limited to:

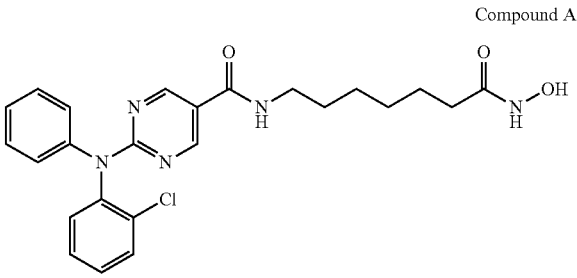

Compound A 2-((2-chlorophenyl)(phenyl)amino)-N-(7-(hydroxyamino)-7-oxoheptyl)pyrimidine-5-carboxamide $IC_{50}$(nM) HDAC6 = 4 HDAC3 = 76

-continued

Compound B

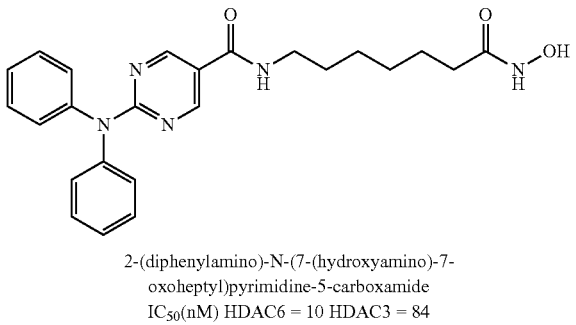

2-(diphenylamino)-N-(7-(hydroxyamino)-7-oxoheptyl)pyrimidine-5-carboxamide
IC$_{50}$(nM) HDAC6 = 10 HDAC3 = 84 or pharmaceutically acceptable salts thereof. In some embodiments, the HDAC6 selective inhibitor is Compound A, or a pharmaceutically acceptable salt thereof. In other embodiments, the HDAC6 selective inhibitor is Compound B, or a pharmaceutically acceptable salt thereof.

The preparation and properties of selective HDAC6 inhibitors according to Formula I are provided in International Patent Application No. PCT/US2011/021982 and PCT/US2014/059238, the entire contents of which are incorporated herein by reference.

CD20 Inhibitory Antibodies

Some embodiments of the pharmaceutical combinations and methods disclosed herein comprise a CD20 inhibitory antibody. Examples of CD20 inhibitory antibodies include, but are not limited to, BLX-301, BVX 20, DXL625, DXLr120, FBTA05, ibritumomab tiuxetan (radiolabeled with yttrium), IGN002 (anti-CD20 monoclonal antibody-interferon alpha fusion), mAB 1.5.3, MEDI-552, MT-3724, obinutuzumab, ocaratuzumab, ocrelizumab, ofatumumab, PRO131921, rituximab, SBI-087 (PF-05230895), tositumomab (radiolabeled with iodine), TRU-015, ublituximab (TG20) and veltuzumab (IMMU-106).

In some embodiments of the methods and the pharmaceutical combinations disclosed herein, the CD20 inhibitory antibody is selected from the group consisting of BLX-301, BVX 20, DXL625, DXLr120, FBTA05, ibritumomab tiuxetan (radiolabeled with yttrium), IGN002 (anti-CD20 monoclonal antibody-interferon alpha fusion), mAB 1.5.3, MEDI-552, MT-3724, obinutuzumab, ocaratuzumab, ocrelizumab, ofatumumab, PRO131921, rituximab, SBI-087 (PF-05230895), tositumomab, TRU-015, ublituximab (TG20) and veltuzumab (IMMU-106). In still another embodiment, the CD20 inhibitory antibody is a biosimilar of rituximab. In certain embodiments, the biosimilar of rituximab is selected from the group consisting of ABP 798, BCD-020, BI 695500, CMAB304, CT-P10, GNR-006, GP2013, Haixi rituximab biosimilar, HLX01, IBI301, MabionCD20, MK-8808, PBO-326, PF-05280586, reditux, RGB-03, RTXM83, SAIT101, SCT400, TL011, and zitux.

In other embodiments, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab. In some embodiments, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab. In certain embodiments, the CD20 inhibitory antibody is selected from the group consisting of obinutuzumab, ocaratuzumab, ocrelizumab, ofatumumab, rituximab, TRU-015, ublituximab, and veltuzumab. In another embodiment, the CD20 inhibitory antibody is selected from the group consisting of obinutuzumab, ocaratuzumab, ocrelizumab, ofatumumab, TRU-015, ublituximab, and veltuzumab.

In some embodiments, the CD20 inhibitory antibody is FBTA05. In another embodiment, the CD20 inhibitory antibody is MT-3724. In yet another embodiment, the CD20 inhibitory antibody is obinutuzumab. In some embodiments, the CD20 inhibitory antibody is ocaratuzumab. In another embodiment, the CD20 inhibitory antibody is ocrelizumab. In still another embodiment, the CD20 inhibitory antibody is ofatumumab. In yet another embodiment, the CD20 inhibitory antibody is PRO131921. In a further embodiment, the CD20 inhibitory antibody is rituximab. In another embodiment, the CD20 inhibitory antibody is SBI-087. In still another embodiment, the CD20 inhibitory antibody is TRU-015. In some embodiments, the CD20 inhibitory antibody is ublituximab. In yet another embodiment, the CD20 inhibitory antibody is veltuzumab.

The CD20 inhibitory antibody comprises three heavy chain complementarity determining regions (CDRs) and three light chain CDRs that bind to CD20. The CD20 inhibitory antibody can comprise a heavy chain variable region and a light chain variable region, which include the respective CDRs. The CD20 inhibitory antibody can comprise a heavy chain and a light chain, which include the respective variable regions.

In one embodiment of the methods and the pharmaceutical combinations disclosed herein, the CD20 inhibitory antibody comprises three heavy chain CDRs set forth in SEQ ID NOs: 1-3 and three light chain CDRs set forth in SEQ ID NOs: 4-6. In another embodiment, the CD20 inhibitory antibody comprises a heavy chain variable region set forth in SEQ ID NO: 7, and a light chain variable region set forth in SEQ ID NO: 8. In yet another embodiment, the CD20 inhibitory antibody comprises a heavy chain variable region set forth in SEQ ID NO: 62, and a light chain variable region set forth in SEQ ID NO: 8. In still another embodiment, the CD20 inhibitory antibody comprises a heavy chain set forth in SEQ ID NO: 9, and a light chain set forth in SEQ ID NO: 10.

In yet another embodiment of the methods and the pharmaceutical combinations disclosed herein, the CD20 inhibitory antibody comprises three heavy chain CDRs set forth in SEQ ID NOs: 11-13 and three light chain CDRs set forth in SEQ ID NOs: 14-16. In some embodiments, the CD20 inhibitory antibody comprises a heavy chain variable region set forth in SEQ ID NO: 17, and a light chain variable region set forth in SEQ ID NO: 18. In another embodiment, the CD20 inhibitory antibody comprises a heavy chain set forth in SEQ ID NO: 19, and a light chain set forth in SEQ ID NO: 20.

In still another embodiment of the methods and the pharmaceutical combinations disclosed herein, the CD20 inhibitory antibody comprises three heavy chain CDRs set forth in SEQ ID NOs: 21-23 and three light chain CDRs set forth in SEQ ID NOs: 24-26. In another embodiment, the CD20 inhibitory antibody comprises a heavy chain variable region set forth in SEQ ID NO: 27, and a light chain variable region set forth in SEQ ID NO: 28. In some embodiments, the CD20 inhibitory antibody comprises a heavy chain set forth in SEQ ID NO: 29, and a light chain set forth in SEQ ID NO: 30.

In other embodiments of the methods and the pharmaceutical combinations disclosed herein, the CD20 inhibitory antibody comprises three heavy chain CDRs set forth in SEQ ID NOs: 31-33 and three light chain CDRs set forth in SEQ ID NOs: 34-36. In another embodiment, the CD20 inhibitory antibody comprises a heavy chain variable region set forth in SEQ ID NO: 37, and a light chain variable region set forth in SEQ ID NO: 38. In some embodiments, the CD20 inhibitory antibody comprises a heavy chain set forth in SEQ ID NO: 39, and a light chain set forth in SEQ ID NO: 40.

In another embodiment of the methods and the pharmaceutical combinations disclosed herein, the CD20 inhibitory antibody comprises three heavy chain CDRs set forth in SEQ ID NOs: 41-43 and three light chain CDRs set forth in SEQ ID NOs: 44-46. In another embodiment, the CD20 inhibitory antibody comprises a heavy chain variable region set forth in SEQ ID NO: 47, and a light chain variable region set forth in SEQ ID NO: 48. In some embodiments, the CD20 inhibitory antibody comprises a heavy chain set forth in SEQ ID NO: 49, and a light chain set forth in SEQ ID NO: 50.

In still another embodiment of the methods and the pharmaceutical combinations disclosed herein, the CD20 inhibitory antibody comprises three heavy chain CDRs set forth in SEQ ID NOs: 1-3 and three light chain CDRs set forth in SEQ ID NOs: 6, 51, and 52. In another embodiment, the CD20 inhibitory antibody comprises a polypeptide set forth in SEQ ID NO: 53.

In still another embodiment of the methods and the pharmaceutical combinations disclosed herein, the CD20 inhibitory antibody comprises three heavy chain CDRs set forth in SEQ ID NOs: 54-56 and three light chain CDRs set forth in SEQ ID NOs: 4, 5, and 57. In another embodiment, the CD20 inhibitory antibody comprises a heavy chain variable region set forth in SEQ ID NO: 58, and a light chain variable region set forth in SEQ ID NO: 59. In some embodiments, the CD20 inhibitory antibody comprises a heavy chain set forth in SEQ ID NO: 60, and a light chain set forth in SEQ ID NO: 61.

In one embodiment of the methods and the pharmaceutical combinations disclosed herein, the CD20 inhibitory antibody comprises three heavy chain CDRs set forth in SEQ ID NOs: 1, 2, and 63 and three light chain CDRs set forth in SEQ ID NOs: 5, 51, and 64. In another embodiment, the CD20 inhibitory antibody comprises a heavy chain variable region set forth in SEQ ID NO: 65, and a light chain variable region set forth in SEQ ID NO: 66. In still another embodiment, the CD20 inhibitory antibody comprises a heavy chain set forth in SEQ ID NO: 67, and a light chain set forth in SEQ ID NO: 68.

In some embodiments, the compounds described herein are unsolvated. In other embodiments, one or more of the compounds are in solvated form. As known in the art, the solvate can be any of pharmaceutically acceptable solvent, such as water, ethanol, and the like.

Although the compounds of Formula I are depicted in their neutral forms, in some embodiments, these compounds are used in a pharmaceutically acceptable salt form.

Pharmaceutical Combinations and Compositions

In an aspect, provided herein is a pharmaceutical combination comprising a histone deacetylase (HDAC) inhibitor and a CD20 inhibitory antibody. In an embodiment, the HDAC inhibitor is an HDAC6 selective inhibitor.

In some embodiments of the pharmaceutical combinations, the HDAC inhibitor is an HDAC6 selective inhibitor. In specific embodiments, the HDAC6 selective inhibitor is a compound of Formula I:

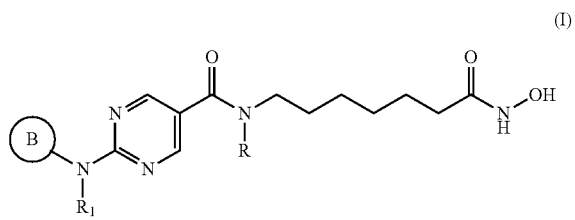

or a pharmaceutically acceptable salt thereof,
wherein
ring B is aryl or heteroaryl;
$R_1$ is an aryl or heteroaryl, each of which may be optionally substituted by OH, halo, or $C_{1-6}$-alkyl;
and
R is H or $C_{1-6}$-alkyl.

In an embodiment of Formula I, $R_1$ is an aryl that is substituted by OH, halo, or $C_{1-6}$-alkyl.

In preferred embodiments, the compound of Formula I is Compound A

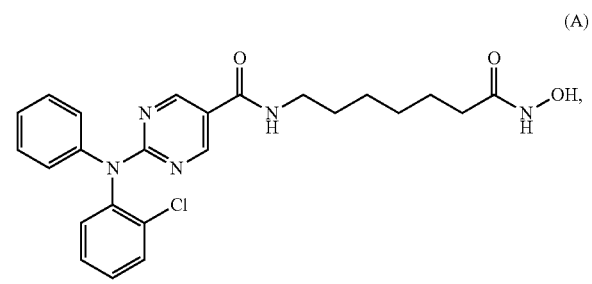 [SMILES: O=C(CCCCCCNC(=O)c1cnc(N(c2ccccc2)c2ccccc2Cl)nc1)NO]

or a pharmaceutically acceptable salt thereof.

In yet other embodiments, the compound of Formula I is Compound B

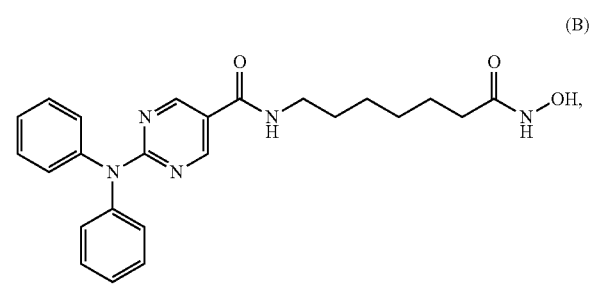 [SMILES: O=C(CCCCCCNC(=O)c1cnc(N(c2ccccc2)c2ccccc2)nc1)NO]

or a pharmaceutically acceptable salt thereof.

In yet another embodiment, the pharmaceutical combination comprises the HDAC inhibitor Compound A, or a pharmaceutically acceptable salt thereof, and a CD20 inhibitory antibody. In other embodiments, the pharmaceutical combination comprises the HDAC inhibitor Compound A, or a pharmaceutically acceptable salt thereof, and a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab. In another embodiment, the pharmaceutical combination comprises the HDAC inhibitor Compound A, or a pharmaceutically acceptable salt thereof, and the CD20 inhibitory antibody rituximab.

In yet another embodiment, the pharmaceutical combination comprises the HDAC inhibitor Compound B, or a pharmaceutically acceptable salt thereof, and a CD20 inhibitory antibody. In still another embodiment, the pharmaceutical combination comprises the HDAC inhibitor Compound B, or a pharmaceutically acceptable salt thereof, and a CD20 inhibitory antibody, wherein the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab. In another embodiment, the pharmaceutical combination comprises the HDAC inhibitor Compound B, or a pharmaceutically acceptable salt thereof, and the CD20 inhibitory antibody rituximab.

Also provided herein are uses of the foregoing pharmaceutical combinations and compositions for the manufacture of a pharmaceutical preparation or medicament for the treatment of a B-cell disorder. In an embodiment, the pharmaceutical combination is for use in the treatment of a B-cell disorder in a subject. In some embodiments, the B-cell disorder is selected from the group consisting of cancer, an autoimmune disorder, and transplant rejection. In another embodiment, the pharmaceutical combination is for use in the treatment of cancer. In certain embodiments, the cancer is resistant or refractory to treatment with the CD20 inhibitory antibody. In another embodiment, the pharmaceutical combination is for use in the treatment of an autoimmune disorder.

In another embodiment, the pharmaceutical combination is for use in the treatment of cancer in a subject, wherein the subject is resistant or refractory to treatment with the CD20 inhibitory antibody.

In an embodiment, the pharmaceutical combination is for use in the treatment of a B-cell disorder in a subject, wherein the subject is treatment naïve.

In an embodiment of the pharmaceutical combination, Compound A is in an amount from 600 mg to 3000 mg (e.g., about 600, about 800, about 1000, about 1200, about 1400, about 1600, about 1800, about 2000 mg). In a further embodiment of the pharmaceutical combination, Compound A is in an amount from 600 mg to 2000 mg.

In another embodiment of the pharmaceutical combination, Compound A is in an amount from 5 mg to 600 mg (e.g., about 5, about 25, about 50, about 100, about 200, about 300, about 400, about 500, about 600 mg). In yet another embodiment of the pharmaceutical combination Compound A is 10 mg to 200 mg.

In an embodiment of the pharmaceutical combination, Compound B is in an amount from 600 mg to 3000 mg (e.g., about 600, about 800, about 1000, about 1200, about 1400, about 1600, about 1800, about 2000 mg). In a further embodiment of the pharmaceutical combination, Compound B is in an amount from 600 mg to 2000 mg.

In another embodiment of the pharmaceutical combination, Compound B is in an amount from 5 mg to 600 mg (e.g., about 5, about 25, about 50, about 100, about 200, about 300, about 400, about 500, about 600 mg). In yet another embodiment of the pharmaceutical combination Compound B is 10 mg to 200 mg.

In an embodiment of the pharmaceutical combination, the CD20 antibody is in an amount from 600 mg to 3000 mg (e.g., about 600, about 800, about 1000, about 1200, about 1400, about 1600, about 1800, about 2000 mg). In a further embodiment of the pharmaceutical combination, the CD20 antibody is in an amount from 600 mg to 2000 mg.

In another embodiment of the pharmaceutical combination, the CD20 antibody is in an amount from 5 mg to 600 mg (e.g., about 5, about 25, about 50, about 100, about 200, about 300, about 400, about 500, about 600 mg). In yet another embodiment of the pharmaceutical combination, the CD20 antibody is 10 mg to 200 mg.

In an embodiment of the pharmaceutical combination, rituximab is in an amount from 600 mg to 3000 mg (e.g., about 600, about 800, about 1000, about 1200, about 1400, about 1600, about 1800, about 2000 mg). In a further embodiment of the pharmaceutical combination, rituximab is in an amount from 600 mg to 2000 mg.

In another embodiment of the pharmaceutical combination, rituximab is in an amount from 5 mg to 600 mg (e.g., about 5, about 25, about 50, about 100, about 200, about 300, about 400, about 500, about 600 mg). In yet another embodiment of the pharmaceutical combination, rituximab is 10 mg to 200 mg.

In certain embodiments of the foregoing pharmaceutical combinations and compositions, when the HDAC inhibitor is Compound B, or a pharmaceutically acceptable salt thereof, the CD20 inhibitory antibody is not rituximab. In some embodiments, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab. In other embodiments, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

In an embodiment of the pharmaceutical combination, the ratio of HDAC6 selective inhibitor to CD20 antibody is in the range of 700:1-1:40. In another embodiment, the ratio of HDAC6 selective inhibitor to CD20 antibody is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Formula I to CD20 antibody is in the range of 700:1-1:40. In another embodiment, the ratio of HDAC6 selective inhibitor to CD20 antibody is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound A to CD20 antibody is in the range of 700:1-1:40. In another embodiment, the ratio of Compound A to CD20 antibody is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound B to CD20 antibody is in the range of 700:1-1:40. In another embodiment, the ratio of Compound B to CD20 antibody is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In another embodiment of the pharmaceutical combination, the ratio of Compound A to Rituximab is in the range of 700:1-1:40. In another embodiment, the ratio of Compound A to Rituximab is in the range of 2:1 to 1:2, for example, 2:1, 1:1, or 1:2; 170:1 to 150:1, for example, 170:1, 160:1 or 150:1; 3:1 to 1:1, for example, 3:1, 2:1 or 1:1; or 30:1 to 10:1, for example, 30:1, 20:1 or 10:1.

In other embodiments of the foregoing pharmaceutical combinations and compositions, the pharmaceutical combination or composition further comprises one or more pharmaceutically acceptable carriers.

Methods of Use

Methods for Treating a B-Cell Disorder

In one aspect, the disclosure relates to methods for treating a B-cell disorder in a subject in need thereof, comprising administering to the subject a pharmaceutical combination of the disclosure. Thus, provided herein are methods for treating a B-cell disorder in a subject in need thereof comprising administering to the subject a therapeutically effective amount of a pharmaceutical combination comprising an HDAC inhibitor and a CD20 inhibitory antibody. In an embodiment, the HDAC inhibitor is an HDAC6 selective inhibitor.

In one embodiment, provided herein is a method for treating a B-cell disorder in a subject in need thereof, comprising administering to the subject a therapeutically effective amount of an HDAC inhibitor of Formula I, or a pharmaceutically acceptable salt thereof, and a therapeutically effective amount of a CD20 inhibitory antibody. In some embodiments, provided herein is a method for treating a B-cell disorder in a subject in need thereof, comprising administering to the subject a therapeutically effective amount of Compound A, or a pharmaceutically acceptable salt thereof, and a therapeutically effective amount of a CD20 inhibitory antibody.

In another embodiment is a method for treating a B-cell disorder in a subject in need thereof, comprising administering to the subject a therapeutically effective amount of Compound A, or a pharmaceutically acceptable salt thereof, and a therapeutically effective amount of rituximab. This embodiment exhibits synergy such that sub-therapeutic amounts of Compound A or of rituximab can be used in the method.

In yet another embodiment is a method for treating a B-cell disorder in a subject in need thereof, comprising administering to the subject a therapeutically effective amount of Compound A, or a pharmaceutically acceptable salt thereof, and a therapeutically effective amount of a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

In other embodiments, provided herein is a method for treating a B-cell disorder in a subject in need thereof, comprising administering to the subject a therapeutically effective amount of Compound B, or a pharmaceutically acceptable salt thereof, and a therapeutically effective amount of a CD20 inhibitory antibody. In some embodiments, the method comprises administering to the subject a therapeutically effective amount of Compound B, or a pharmaceutically acceptable salt thereof, and a therapeutically effective amount of the CD20 inhibitory antibody selected from the group consisting of FBTA05, MT-3724, obinutuzumab, ocaratuzumab, ocrelizumab, ofatumumab, PRO131921, SBI-087, TRU-015, ublituximab, and veltuzumab.

In some embodiments, the B-cell disorder is selected from the group consisting of cancer, an autoimmune disorder, and transplant rejection. In other embodiments, the B-cell disorder is an autoimmune disorder or transplant rejection.

In other embodiments, the B-cell disorder is an autoimmune disorder. In another embodiment, the autoimmune disorder is selected from anti-N-methyl D-aspartate (NMDA) receptor encephalitis, autoimmune anemia, autoimmune pancreatitis, bullous skin disorders, chronic inflammatory demyelinating polyneuropathy, Evans syndrome, Graves' ophthalmopathy, idiopathic thrombocytopenic purpura (ITP), IgG4-related disease, pure red cell aplasia, multiple sclerosis, neuromyelitis optica (Devic's disease), opsoclonus myoclonus syndrome (OMS), rheumatoid arthritis, Sjogren's syndrome, systemic lupus erythematosus, thrombotic thrombocytopenic purpura (TTP), type 1 diabetes mellitus, and vasculitis. In yet another embodiment, the vasculitis is granulomatosis with polyangiitis (GPA) (Wegner's granulomatosis) or microscopic polyangiitis (MPA).

In other embodiments of the foregoing methods, the viability of a peripheral blood mononuclear cell is maintained. In some embodiments, the peripheral blood mononuclear cell is a CD20+ B lymphocyte, a CD20+ follicular B lymphocyte, or a CD20+ diffuse large B-cell.

In another aspect, the disclosure relates to methods for upregulating antibody-dependent cell-mediated cytotoxicity in a subject in need thereof. In particular, the disclosure relates to methods for upregulating antibody-dependent cell-mediated cytotoxicity in a subject in need thereof, comprising administering to the subject a therapeutically effective amount of an HDAC inhibitor of Formula I, or a pharmaceutically acceptable salt thereof, and a CD20 inhibitory antibody. In some embodiments, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab. In other embodiments, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab.

In some embodiments is a method for upregulating antibody-dependent cell-mediated cytotoxicity in a subject in need thereof, comprising administering to the subject a therapeutically effective amount of Compound A, or a pharmaceutically acceptable salt thereof, and a CD20 inhibitory antibody. In some embodiments, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab. In another embodiment the method for upregulating antibody-dependent cell-mediated cytotoxicity in a subject in need thereof comprises administering to the subject a therapeutically effective amount of Compound A, or a pharmaceutically acceptable salt thereof, and rituximab.

In another embodiment, the disclosure relates to methods for upregulating antibody-dependent cell-mediated cytotoxicity in a subject in need thereof, comprising administering to the subject a therapeutically effective amount of Compound B, or a pharmaceutically acceptable salt thereof, and a CD20 inhibitory antibody. In some embodiments, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab. In another embodiment the method for upregulating antibody-dependent cell-mediated cytotoxicity in a subject in need thereof comprises administering to the subject a therapeutically effective amount of Compound B, or a pharmaceutically acceptable salt thereof, and rituximab.

In still another aspect, the disclosure relates to methods for upregulating lymphocyte functional activity in a subject in need thereof. Specifically, the disclosure relates to methods for upregulating lymphocyte functional activity in a subject in need thereof, comprising administering to the subject a therapeutically effective amount of an HDAC inhibitor of Formula I, or a pharmaceutically acceptable salt thereof, and a CD20 inhibitory antibody.

In yet another embodiment is a method for upregulating lymphocyte functional activity in a subject in need thereof, comprising administering to the subject a therapeutically effective amount of Compound A, or a pharmaceutically acceptable salt thereof, and a CD20 inhibitory antibody. In some embodiments, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab. In another embodiment the method for upregulating lymphocyte functional activity in a subject in need thereof comprises administering to the subject a therapeutically effective amount of Compound A, or a pharmaceutically acceptable salt thereof, and rituximab.

In still another embodiment is a method for upregulating lymphocyte functional activity in a subject in need thereof, comprising administering to the subject a therapeutically effective amount of Compound B, or a pharmaceutically acceptable salt thereof, and a CD20 inhibitory antibody. In some embodiments, the CD20 inhibitory antibody is selected from the group consisting of FBTA05, MT-3724, obinutuzumab, ocaratuzumab, ocrelizumab, ofatumumab, PRO131921, SBI-087, TRU-015, ublituximab, and veltuzumab. In another embodiment the method for upregulating lymphocyte functional activity in a subject in need thereof comprises administering to the subject a therapeutically effective amount of Compound B, or a pharmaceutically acceptable salt thereof, and rituximab.

In a further embodiment, the lymphocyte is a natural killer cell. In other embodiments, the lymphocyte is a T lymphocyte. In another embodiment, the lymphocyte is a B lymphocyte. In still another embodiment, the B lymphocyte is a follicular B lymphocyte. In other embodiments, the B lymphocyte is a diffuse large B-cell.

In still another aspect, the disclosure relates to methods of upregulating the expression of CD20 in a cell. In particular, the disclosure relates to methods of upregulating the expression of CD20 in a cell comprising contacting the cell with an HDAC inhibitor. In one embodiment is a method of upregulating the expression of CD20 in a cell comprising contacting the cell with an HDAC inhibitor of Formula I, or a pharmaceutically acceptable salt thereof. In another embodiment is a method of upregulating the expression of CD20 in a cell comprising contacting the cell with Compound A, or a pharmaceutically acceptable salt thereof. In another embodiment is a method of upregulating the expression of CD20 in a cell comprising contacting the cell with Compound B, or a pharmaceutically acceptable salt thereof.

In certain embodiments of the foregoing methods, when the HDAC inhibitor is Compound B, or a pharmaceutically acceptable salt thereof, the CD20 inhibitory antibody is not rituximab. In some embodiments, the CD20 inhibitory antibody is selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

Methods for Treating Cancer

In another aspect, the disclosure provides methods for treating cancer in a subject in need thereof, comprising administering to the subject a therapeutically effective amount of a pharmaceutical combination comprising an HDAC inhibitor and a CD20 inhibitory antibody. In an embodiment, the HDAC inhibitor is an HDAC6 selective inhibitor.

In one embodiment, provided herein is a method for treating cancer in a subject in need thereof, comprising administering to the subject a therapeutically effective amount of an HDAC inhibitor of Formula I, or a pharmaceutically acceptable salt thereof, and a therapeutically effective amount of a CD20 inhibitory antibody. In some embodiments, provided herein is a method for treating cancer in a subject in need thereof, comprising administering to the subject a therapeutically effective amount of Compound A, or a pharmaceutically acceptable salt thereof, and a therapeutically effective amount of a CD20 inhibitory antibody.

In another embodiment is a method for treating cancer in a subject in need thereof, comprising administering to the subject a therapeutically effective amount of Compound A, or a pharmaceutically acceptable salt thereof, and a therapeutically effective amount of rituximab. This embodiment exhibits synergy such that sub-therapeutic amounts of Compound A can be used in the method.

In yet another embodiment is a method for treating cancer in a subject in need thereof, comprising administering to the subject a therapeutically effective amount of Compound A, or a pharmaceutically acceptable salt thereof, and a therapeutically effective amount of a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

In other embodiments, provided herein is a method for treating cancer in a subject in need thereof, comprising administering to the subject a therapeutically effective amount of Compound B, or a pharmaceutically acceptable salt thereof, and a therapeutically effective amount of a CD20 inhibitory antibody. In some embodiments, the method comprises administering to the subject a therapeutically effective amount of Compound B, or a pharmaceutically acceptable salt thereof, and a therapeutically effective amount of the CD20 inhibitory antibody selected from the group consisting of FBTA05, MT-3724, obinutuzumab, ocaratuzumab, ocrelizumab, ofatumumab, PRO131921, SBI-087, TRU-015, ublituximab, and veltuzumab.

In some embodiments, the cancer is a B-cell disorder. In another embodiment, the cancer is a leukemia, a lymphoma, or a myeloma. In a further embodiment, the cancer is multiple myeloma. In another embodiment, the cancer is a hematologic malignancy. In yet another embodiment, the cancer is selected from the group consisting of acute lymphoblastic leukemia, B-cell leukemia, chronic lymphocytic leukemia, acute myeloid leukemia, chronic myeloid leukemia, B-cell lymphoma, Burkitt lymphoma, diffuse large B-cell lymphoma, non-Hodgkin's lymphoma, lymphocyte predominant subtype of Hodgkin's lymphoma, mantle cell lymphoma, and multiple myeloma. In still another embodiment, the cancer is selected from the group consisting of chronic lymphocytic leukemia, non-Hodgkin's lymphoma, and multiple myeloma. In another embodiment, the cancer is multiple myeloma.

In some embodiments of the methods disclosed herein, the cell is a cancer cell. In another embodiment, the cell is a chronic lymphocytic leukemia cell. In still another embodiment, the cell is a non-Hodgkin's lymphoma cell. In yet another embodiment, the cell is a multiple myeloma cell.

In certain embodiments of the foregoing methods, the expression of CD20 on a cancer cell is upregulated. In some embodiments, the expression of CD20 on a chronic lymphocytic leukemia cell is upregulated. In another embodiment, the expression of CD20 on a non-Hodgkin's lymphoma cell is upregulated. In still another embodiment, the expression of CD20 on a multiple myeloma cell is upregulated.

In some embodiments of the foregoing methods, the cancer or the cancer cell is resistant or refractory to treatment with the CD20 inhibitory antibody. In another embodiment, the chronic lymphocytic leukemia is resistant or refractory to treatment with the CD20 inhibitory antibody. In still another embodiment, the non-Hodgkin's lymphoma is resistant or refractory to treatment with the CD20 inhibitory antibody. In yet another embodiment, the multiple myeloma is resistant or refractory to treatment with the CD20 inhibitory antibody. In further embodiments of the methods disclosed herein, the cancer is resistant or refractory to treatment with a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab. In other embodiments of the methods disclosed herein, the cancer is resistant or refractory to treatment with rituximab.

The subject considered herein is typically a human. However, the subject can be any mammal for which treatment is desired. Thus, the methods described herein can be applied to both human and veterinary applications.

Administration/Dose

In some embodiments, the HDAC6 selective inhibitor (a compound of Formula I) is administered simultaneously with the CD20 inhibitory antibody. Simultaneous administration typically means that both compounds enter the patient at precisely the same time. However, simultaneous administration also includes the possibility that the HDAC6 selective inhibitor and the CD20 inhibitory antibody enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the pharmaceutical combination of compounds. In another example, simultaneous administration of separate solutions, one of which contains the HDAC6 selective inhibitor and the other of which contains the CD20 inhibitory antibody, can be employed. In one example wherein the compounds are in solid form, simultaneous administration can be achieved by administering a composition containing the pharmaceutical combination of compounds. Alternatively, simultaneous administration can be achieved by administering two separate compositions, one comprising the HDAC6 selective inhibitor and the other comprising the CD20 inhibitory antibody.

In some embodiments, the pharmaceutical combination of compounds exhibits a synergistic effect (i.e., greater than additive effect) in the treatment of a B-cell disorder, such as a cancer, an autoimmune disorder, or a transplant rejection. The term "synergistic effect" refers to the action of two agents, such as, for example, an HDAC6 selective inhibitor and a CD20 inhibitory antibody, producing an effect, for example, slowing the symptomatic progression of cancer or symptoms thereof, which is greater than the simple addition of the effects of each drug administered by themselves. A synergistic effect can be calculated, for example, using suitable methods such as the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied to experimental data to generate a corresponding graph to aid in assessing the effects of the drug combination. The corresponding graphs associated with the equations referred to above are the concentration-effect curve, isobologram curve and combination index curve, respectively.

The HDAC6 selective inhibitor and the CD20 inhibitory antibody can be administered independently, at the same time or separately within time intervals, wherein these time intervals allow that the combination partners show a cooperative, e.g., synergistic, effect.

In an embodiment, when the HDAC6 selective inhibitor and the CD20 inhibitory antibody are not administered simultaneously, the two agents exhibit a synergistic effect. In some embodiments, the HDAC6 selective inhibitor is administered before the CD20 inhibitory antibody. In other embodiments, the CD20 inhibitory antibody is administered before the HDAC6 selective inhibitor. The time difference in non-simultaneous administrations can be greater than 1 minute, five minutes, 10 minutes, 15 minutes, 30 minutes, 45 minutes, 60 minutes, two hours, three hours, six hours, nine hours, 12 hours, 24 hours, 36 hours, 48 hours, 3 days, 4 days, 5 days, 6 days, 7 days, 2 weeks, 3 weeks, 4 weeks, 2 months, 3 months, 4 months, 5 months, 6 months, and 7 months. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient. In another embodiment, the HDAC6 selective inhibitor and the CD20 inhibitory antibody are administered at different times.

In some embodiments, the HDAC6 selective inhibitor and the CD20 inhibitory antibody are together formulated as a single formulation.

In other embodiments, the HDAC inhibitor and the CD20 inhibitory antibody are each formulated as separate formulations.

In some embodiments, one or both of the HDAC6 selective inhibitor and the CD20 inhibitory antibody are administered in a therapeutically effective amount or dosage. A "therapeutically effective amount" is an amount of an HDAC6 selective inhibitor (a compound of Formula I or II) or of a CD20 inhibitory antibody that, when administered to a patient by itself, effectively treats cancer. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts of these compounds are well-known in the art, such as provided in the supporting references cited above.

In other embodiments, one or both of the HDAC6 selective inhibitor and the CD20 inhibitory antibody are administered in a sub-therapeutically effective amount or dosage. A sub-therapeutically effective amount is an amount of HDAC6 selective inhibitor (a compound of Formula I or II) or a CD20 inhibitory antibody that, when administered to a patient by itself, does not completely inhibit over time the biological activity of the intended target.

Thus, in one embodiment, an HDAC6 selective inhibitor or a CD20 inhibitory antibody are administered in an amount that would not be effective when one or both of the HDAC6 selective inhibitor and the CD20 inhibitory antibody is administered alone, but which amounts are effective in combination.

Whether administered in therapeutic or sub-therapeutic amounts, the pharmaceutical combination of the HDAC6 selective inhibitor and the CD20 inhibitory antibody should be effective in treating cancer. For example, a sub-therapeutic amount of a compound of the CD20 inhibitory antibody can be an effective amount if, when combined with a compound of Formula I (HDAC6 selective inhibitor), the pharmaceutical combination is effective in the treatment of cancer.

In certain embodiments of the disclosure, the pharmaceutical combinations and methods include an HDAC6 selective inhibitor of Formula I and a CD20 inhibitory antibody. Thus, in one embodiment, the pharmaceutical combinations and methods include Compound A and a CD20 inhibitory antibody. In another embodiment, the pharmaceutical combinations and methods include Compound B and a CD20 inhibitory antibody. These embodiments exhibit synergy such that sub-therapeutic amounts of the HDAC6 selective inhibitor or of the CD20 inhibitory antibody may be used. In certain embodiments of the disclosure, the pharmaceutical combinations and methods include an HDAC6 selective inhibitor (Compound A or Compound B) and a CD20 inhibitory antibody.

In different embodiments, depending on the pharmaceutical combination and the effective amounts used, the pharmaceutical combination of compounds can inhibit cancer growth, achieve cancer stasis, or even achieve substantial or complete cancer regression.

While the amounts of an HDAC6 selective inhibitor and a CD20 inhibitory antibody should result in the effective treatment of cancer, the amounts, when combined, are preferably not excessively toxic to the patient (i.e., the amounts are preferably within toxicity limits as established by medical guidelines). In some embodiments, either to prevent excessive toxicity and/or provide a more efficacious treatment of cancer, a limitation on the total administered dosage is provided. Typically, the amounts considered herein are per day; however, half-day and two-day or three-day cycles also are considered herein.

Different dosage regimens may be used to treat cancer. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) may be employed along with a high dosage, or a longer treatment time (e.g., ten or more days, or weeks, or months, or longer) may be employed along with a low dosage. For example, the CD20 inhibitory antibody can be dosed every week, every 21 days, every 28 days, every two months, every 16 weeks, or every 24 weeks. In some embodiments, a once- or twice-daily dosage is administered every other day. In some embodiments, each dosage contains both an HDAC6 selective inhibitor and a CD20 inhibitory antibody to be delivered as a single dosage, while in other embodiments, each dosage contains either an HDAC6 selective inhibitor and a CD20 inhibitory antibody to be delivered as separate dosages.

The HDAC6 selective inhibitors, the CD20 inhibitory antibodys, or their pharmaceutically acceptable salts or solvate forms, in pure form or in an appropriate pharmaceutical composition, can be administered via any of the accepted modes of administration or agents known in the art. The compounds can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As discussed above, the HDAC6 selective inhibitor and the CD20 inhibitory antibody of the pharmaceutical combination can be administered in a single unit dose or separate dosage forms. Accordingly, the phrase "pharmaceutical combination" includes a combination of two drugs in either a single dosage form or separate dosage forms, i.e., the pharmaceutically acceptable carriers and excipients described throughout the application can be combined with an HDAC6 selective inhibitor and a CD20 inhibitory antibody in a single unit dose, as well as individually combined with an HDAC6 selective inhibitor and a CD20 inhibitory antibody when these compounds are administered separately.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents. Isotonic agents may also be included. Prolonged absorption of an injectable pharmaceutical form can be brought about by the use of agents delaying absorption. The auxiliary agents also can include wetting agents, emulsifying agents, pH buffering agents, and antioxidants.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC6 selective inhibitors or CD20 inhibitory antibodys described herein, or a pharmaceutically acceptable salt thereof, and optional pharmaceutical adjuvants in a carrier to thereby form a solution or suspension.

Generally, depending on the intended mode of administration, the pharmaceutically acceptable compositions will contain about 1% to about 99% by weight of the compounds described herein, or a pharmaceutically acceptable salt thereof, and 99% to 1% by weight of a pharmaceutically acceptable excipient. In one example, the composition will be between about 5% and about 75% by weight of a compound described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising compounds or compositions of the disclosure. In some embodiments, kits comprise an HDAC6 selective inhibitor, or a pharmaceutically acceptable salt thereof, and a CD20 inhibitory antibody.

The phrase "package" means any vessel containing compounds or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering compounds or compositions of the disclosure to a patient. Kits also can comprise instructions for approved uses of compounds herein by regulatory agencies, such as the United States Food and Drug Administration. Kits can also contain labeling or product inserts for the compounds. The package(s) and/or any product insert(s) may themselves be approved by regulatory agencies. The kits can include compounds in the solid phase or in a liquid phase (such as buffers provided) in a package. The kits can also include buffers for preparing solutions for conducting the methods, and pipettes for transferring liquids from one container to another.

EXAMPLES

Examples have been set forth below for the purpose of illustration and to describe certain specific embodiments. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations and/or methods of the disclosure may be made without departing from the spirit of the disclosure and the scope of the appended claims. Definitions of the variables in the structures in the schemes herein are commensurate with those of corresponding positions in the formulae presented herein.

The synthesis of the compounds of Formula I is provided in International Patent Application Nos. PCT/US2011/021982 (Compound A) and PCT/US2014/059238 (Compounds A and B), which are incorporated herein by reference in their entireties.

Example 1: Synthesis of 2-((2-chlorophenyl)(phenyl)amino)-N-(7-(hydroxyamino)-7-oxoheptyl)pyrimidine-5-carboxamide (Compound A)

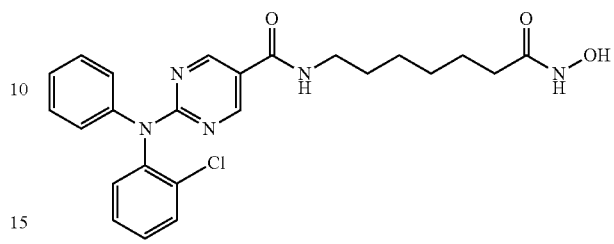

Reaction Scheme

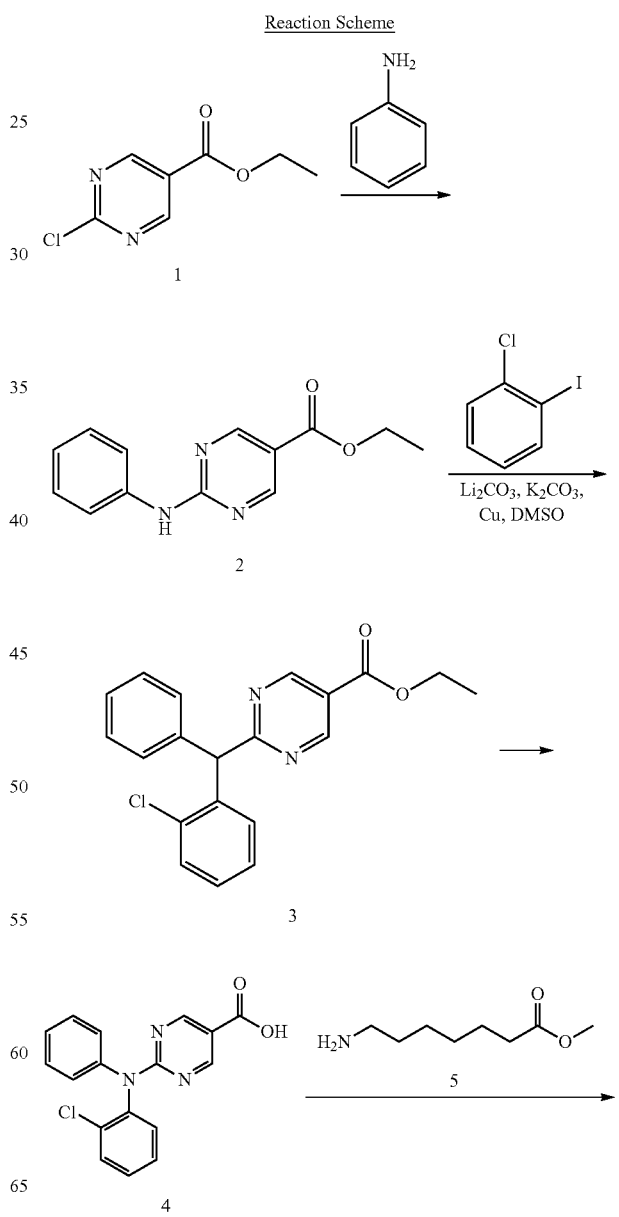

-continued

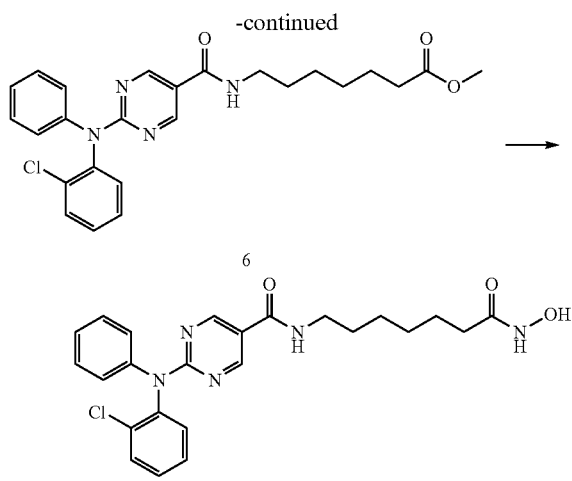

6

Synthesis of Intermediate 2:

A mixture of aniline (3.7 g, 40 mmol), compound 1 (7.5 g, 40 mmol), and K₂CO₃ (11 g, 80 mmol) in DMF (100 ml) was degassed and stirred at 120° C. under N₂ overnight. The reaction mixture was cooled to r.t. and diluted with EtOAc (200 ml), then washed with saturated brine (200 ml×3). The organic layers were separated and dried over Na₂SO₄, evaporated to dryness and purified by silica gel chromatography (petroleum ethers/EtOAc=10/1) to give the desired product as a white solid (6.2 g, 64%).

Synthesis of Intermediate 3:

A mixture of compound 2 (69.2 g, 1 equiv.), 1-chloro-2-iodobenzene (135.7 g, 2 equiv.), Li₂CO₃ (42.04 g, 2 equiv.), K₂CO₃ (39.32 g, 1 equiv.), Cu (1 equiv. 45 μm) in DMSO (690 ml) was degassed and purged with nitrogen. The resulting mixture was stirred at 140° C. Work-up of the reaction gave compound 3 at 93% yield.

Synthesis of Intermediate 4:

2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na₂SO₄. Removal of the solvent gave a brown solid (2.5 g, 92%).

Synthesis of Intermediate 6:

A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-((2-chlorophenyl)(phenyl)amino)-N-(7-(hydroxyamino)-7-oxoheptyl)pyrimidine-5-carboxamide (Compound A)

A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

Example 2: Synthesis of 2-(diphenylamino)-N-(7-(hydroxyamino)-7-oxoheptyl) pyrimidine-5-carboxamide (Compound B)

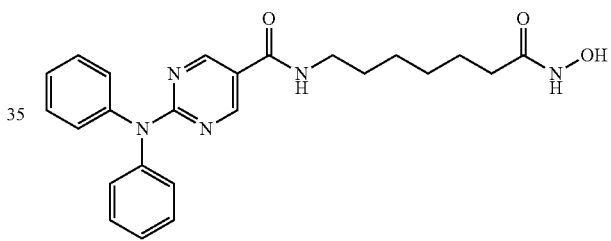

Reaction Scheme

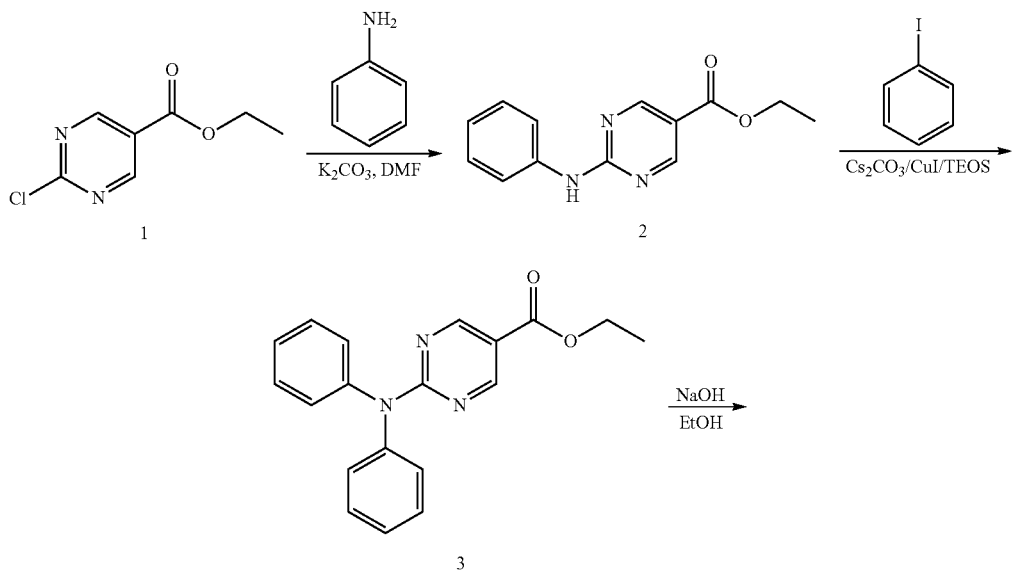

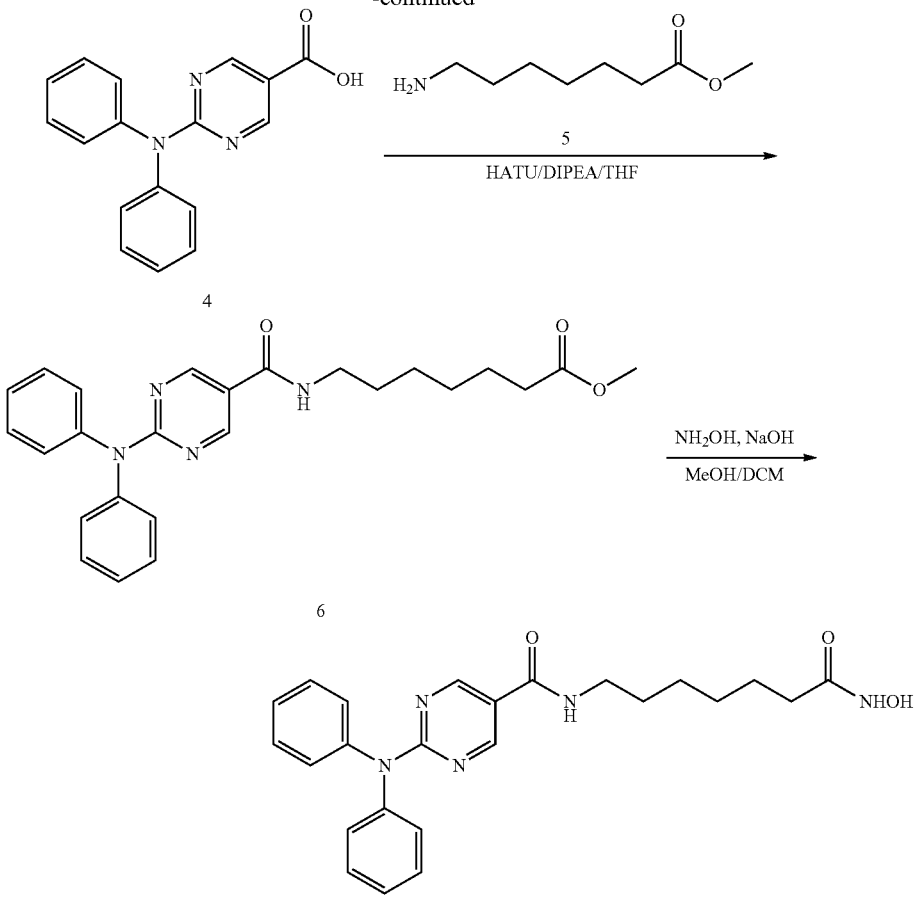

Synthesis of Intermediate 2:
See synthesis of intermediate 2 in Example 1.
Synthesis of Intermediate 3:
A mixture of compound 2 (6.2 g, 25 mmol), iodobenzene (6.12 g, 30 mmol), CuI (955 mg, 5.0 mmol), Cs$_2$CO$_3$ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and NH$_4$F—H$_2$O on silica gel [50 g, pre-prepared by the addition of NH$_4$F (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).
Synthesis of Intermediate 4:
See synthesis of intermediate 4 in Example 1.
Synthesis of Intermediate 6:
See synthesis of intermediate 6 in Example 1.

Synthesis of 2-(diphenylamino)-N-(7-(hydroxyamino)-7-oxoheptyl)pyrimidine-5-carboxamide (Compound B)

See synthesis of Compound A in Example 1.

Example 3: HDAC Enzyme Assays

Compounds for testing were diluted in DMSO to 50 fold the final concentration and a ten point three fold dilution series was made. The compounds were diluted in assay buffer (50 mM HEPES, pH 7.4, 100 mM KCl, 0.001% Tween-20, 0.05% BSA, 20 µM Tris (2-carboxyethyl) phosphine) to 6 fold their final concentration. The HDAC enzymes (purchased from BPS Biosciences) were diluted to 1.5 fold their final concentration in assay buffer. The dipeptide substrate and trypsin at 0.05 µM final concentration were diluted in assay buffer at 6 fold their final concentration. The final enzyme concentrations used in these assays were 3.3 ng/ml (HDAC1), 0.2 ng/ml (HDAC2), 0.08 ng/ml (HDAC3) and 2 ng/ml (HDAC6). The final substrate concentrations used were 16 µM (HDAC1), 10 µM (HDAC2), 17 µM (HDAC3) and 14 µM (HDAC6). Five µl of compound and 20 µl of enzyme were added to wells of a black, opaque 384 well plate in duplicate. Enzyme and compound were incubated together at room temperature for 10 min. Five µl of substrate was added to each well, the plate was shaken for 60 seconds and placed into a Victor 2 microliter plate reader. The development of fluorescence was monitored for 60 min. and the linear rate of the reaction was calculated. The IC$_{50}$ was determined using Graph Pad Prism by a four parameter curve fit.

Figure 1B:
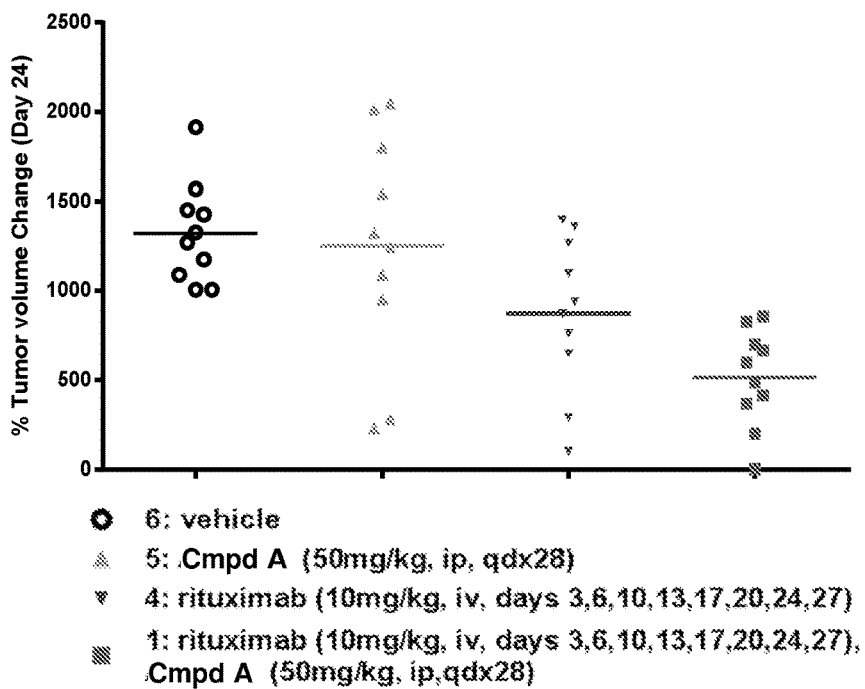
FIG. 1B shows the percentage of tumor volume change at day 24 compared to the average volume of the vehicle group on day 1 (100%).

Example 4: Combination Treatment with Compound A and Rituximab in Burkitt's Lymphoma Cells CB.17 SCID mice were implanted with 1×10$^7$ Raji tumor cells subcutaneously in the flank. Raji tumor cells are from a human lymphoblast tissue (B lymphocyte cells) and model Burkitt's Lymphoma. When tumors reach an average size of 100-150 mm³, mice were treated with vehicle, Compound A (Cmpd A, 50 mg/kg, IP, qd×28), rituximab (10 mg/kg, iv, biweekly), or the combination of Compound A and rituximab for up to 4 weeks. Tumors were measured by caliper biweekly and tumor volumes were calculated as length×width²/2. Mice were euthanized when their tumor volumes reached 2000 mm³. Tumor volume was monitored until the first mouse was euthanized. FIG. 1A shows tumor growth kinetics after treatment with the indicated drugs and antibodies. The combination treatment (Compound A and rituximab) significantly inhibited tumor growth. FIG. 1B shows the percentage of tumor volume change. This was calculated as tumor volume relative to average volume of the vehicle group on day 1 (100%). Combination treatment significantly reduced tumor volumes relative to each single agent. That is, the combination treatment with Compound A and rituximab showed synergistic effects in a model of Burkitt's Lymphoma in comparison to each single agent treatment.

Example 5: Compound A in Raji Cells

Figure 2A:
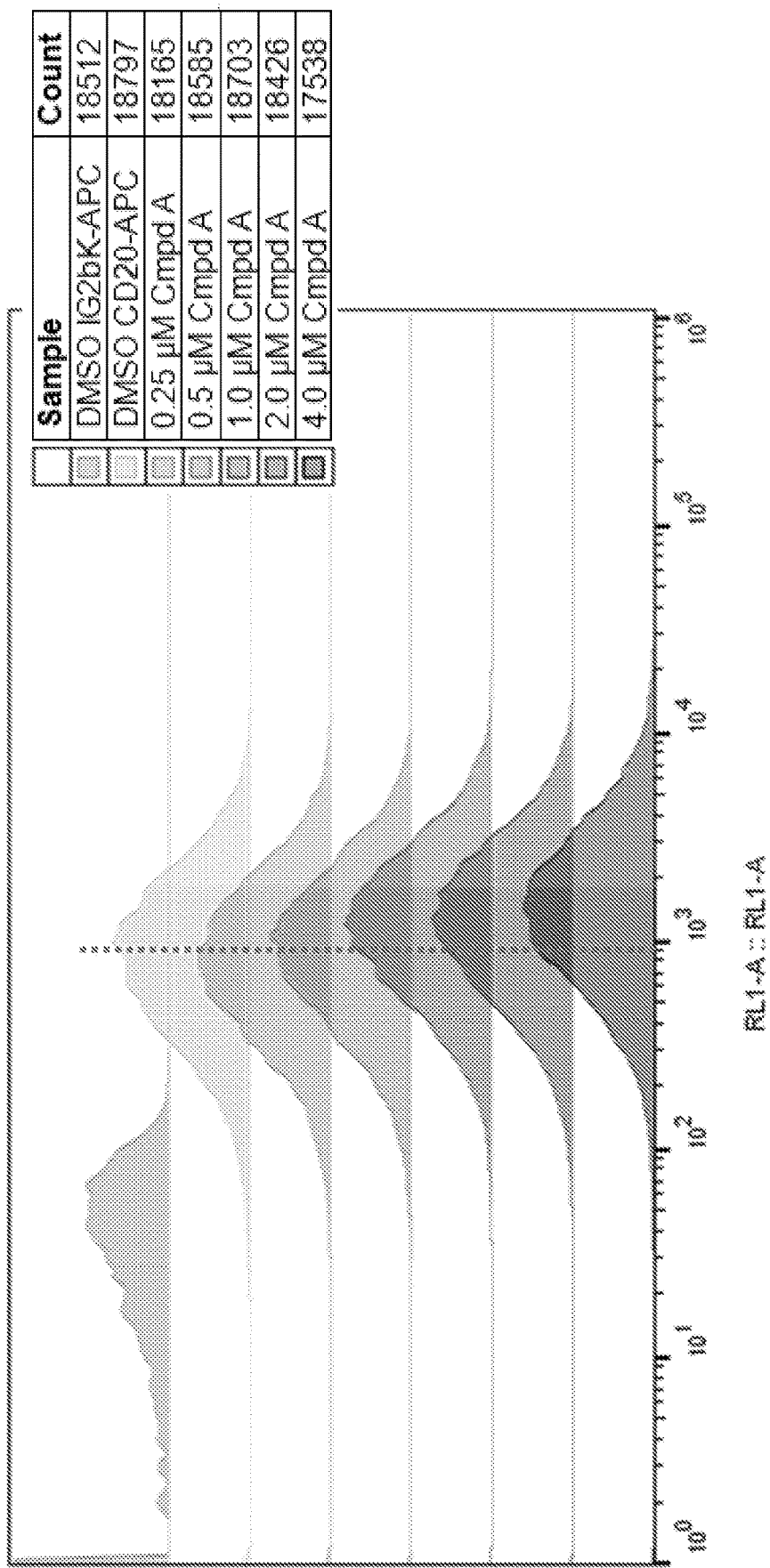
FIG. 2A shows histogram plots of representative samples of Raji cells for each concentration stained for CD20-APC. Dotted line indicates the median of DMSO treatment.
Figure 2B:
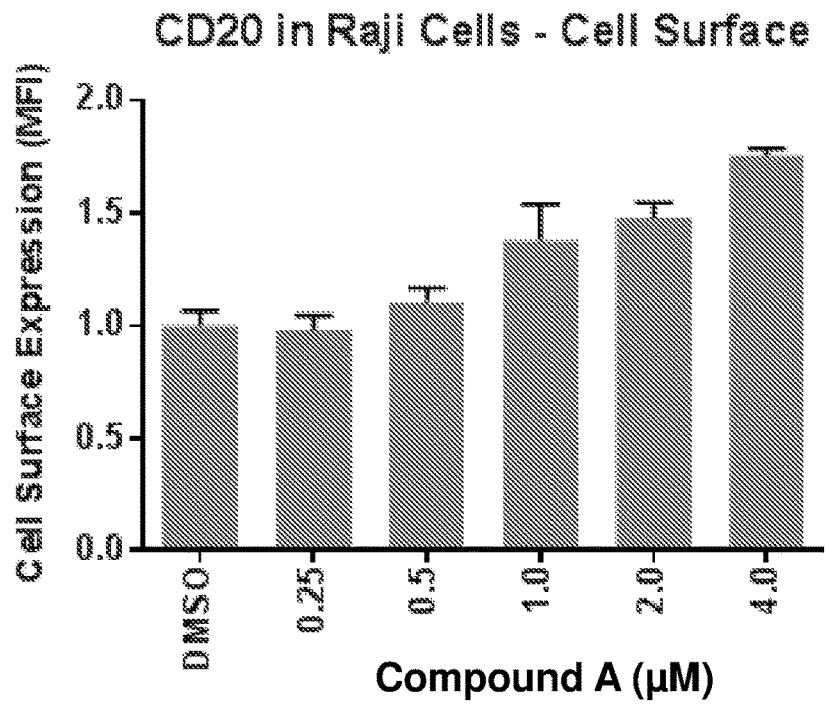
FIG. 2B shows the quantification of mean fluorescence intensity following cell surface staining and flow cytometry showing the levels of CD20 in Raji cells.
Figure 2C:
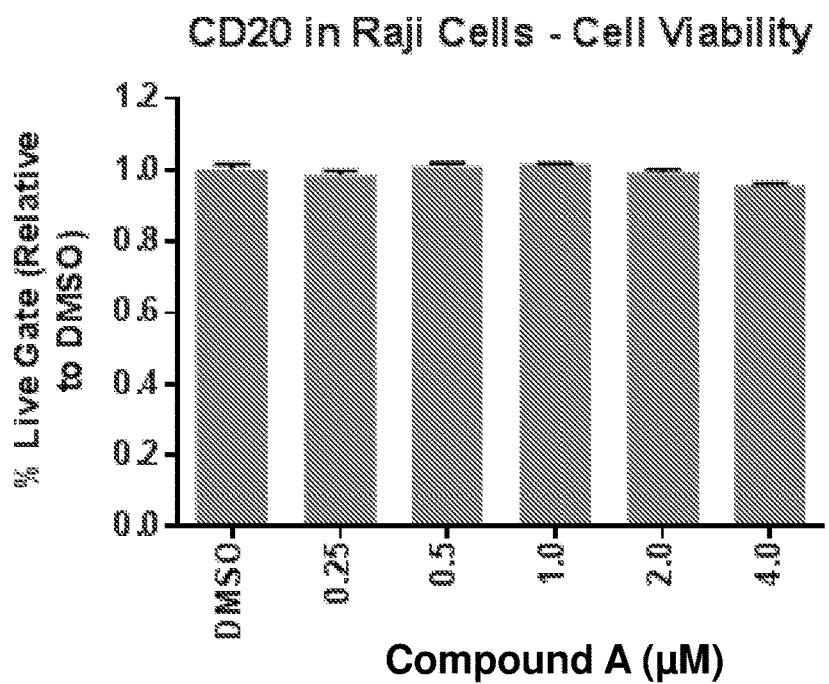
FIG. 2C shows the percentage of live cells as determined by fraction of total cells that were negative for the live/dead viability dye in Raji cells.
Figure 2D:
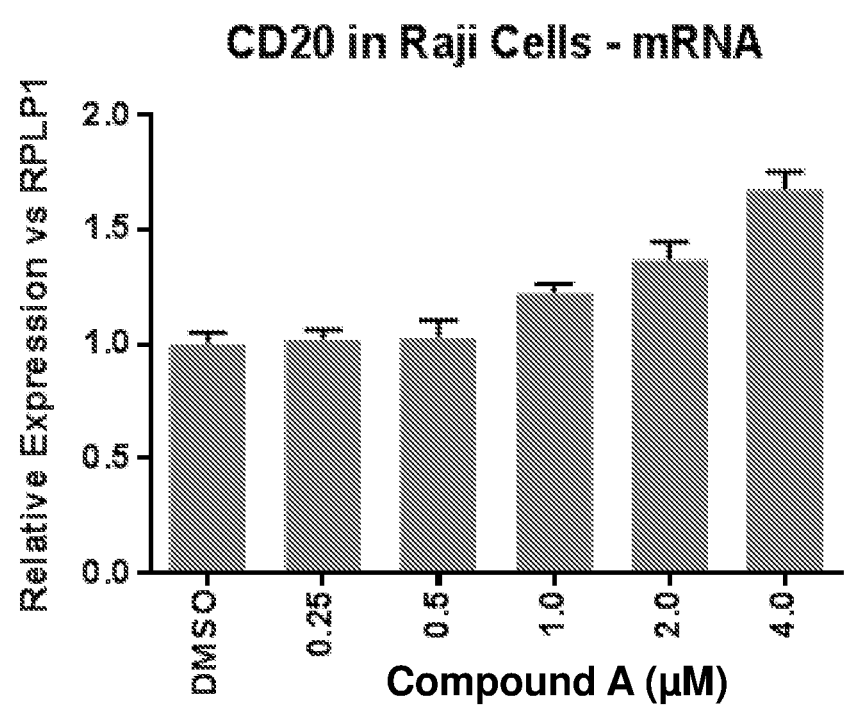
FIG. 2D shows the CD20 mRNA expression relative to RPLP1 in Raji cells.

Cells were treated with increasing concentrations of Compound A (i.e., 0.25 µM, 0.5 µM, 1.0 µM, 2.0 µM, and 4.0 µM) for 48 hours and processed for cell surface abundance of CD20 protein and mRNA in Raji cells. The treated Raji cells were stained for IgG2bK-APC and CD20-APC. FACS histogram plots of a representative sample in Raji cells for each concentration are shown in FIG. 2A. The dotted line indicates median of DMSO treatment. The quantification of mean fluorescence intensity (MFI) following cell surface staining and flow cytometry of Raji cells is shown in FIG. 2B. Each sample was background subtracted, where the IgG2bK-APC median MFI in Raji cells was used as the background. FIG. 2C shows the cell viability as measured by percentage of cells in live gate, relative to DMSO in Raji cells. FIG. 2D shows CD20 mRNA expression relative to RPLP1 in Raji cells. Together, increased CD20 expression triggered by Compound A can be a potential mechanism for the in vivo combination effect on the Raji cell model. Compound A induced CD20 mRNA expression and cell surface abundance of CD20 on Raji cells. That can be a potential mechanism for the synergistic effect of Compound A with rituximab.

Example 6: Compound A in Jeko Cells

Figure 3A:
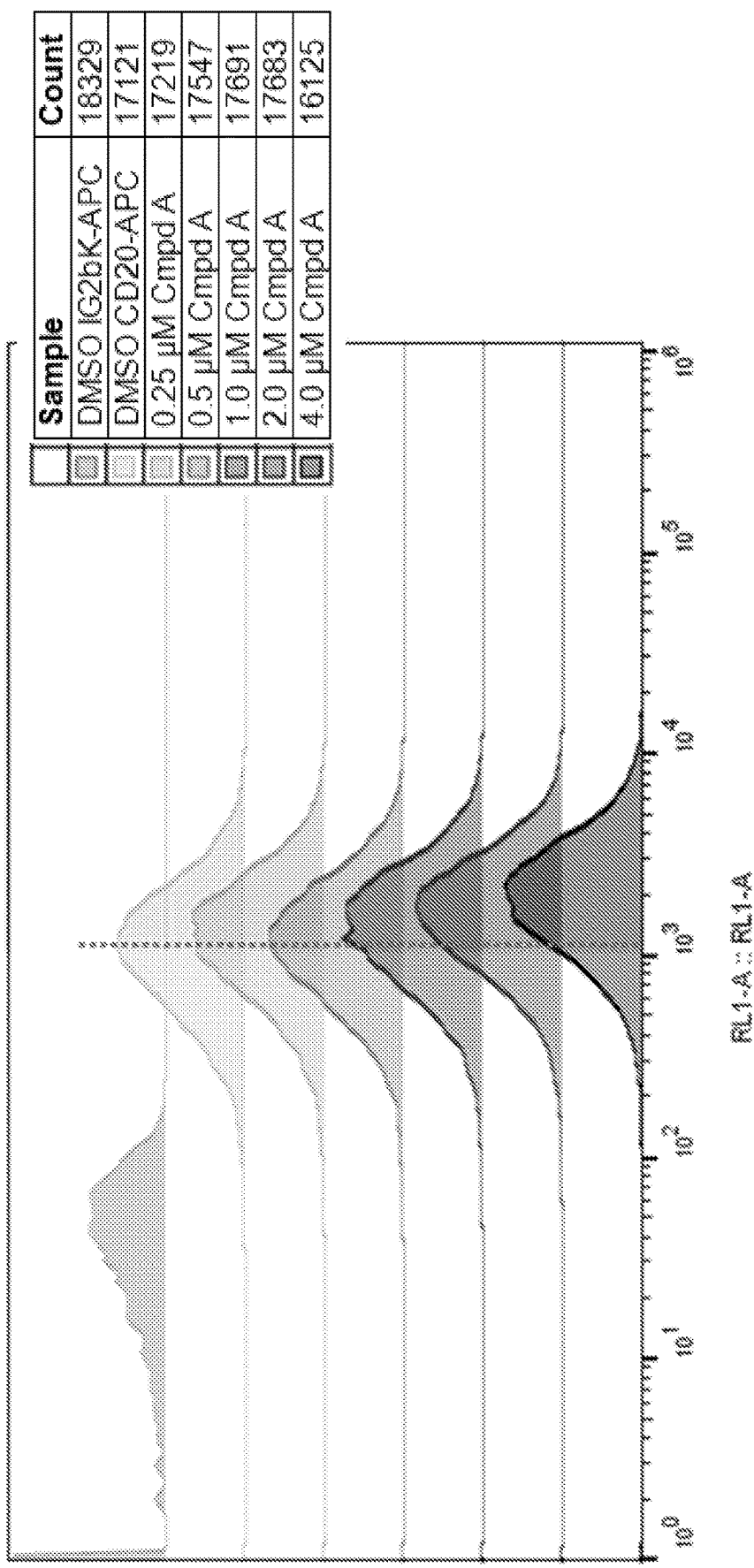
FIG. 3A shows histogram plots of representative samples of Jeko cells for each concentration stained for CD20-APC. Dotted line indicates the median of DMSO treatment.
Figure 3B:
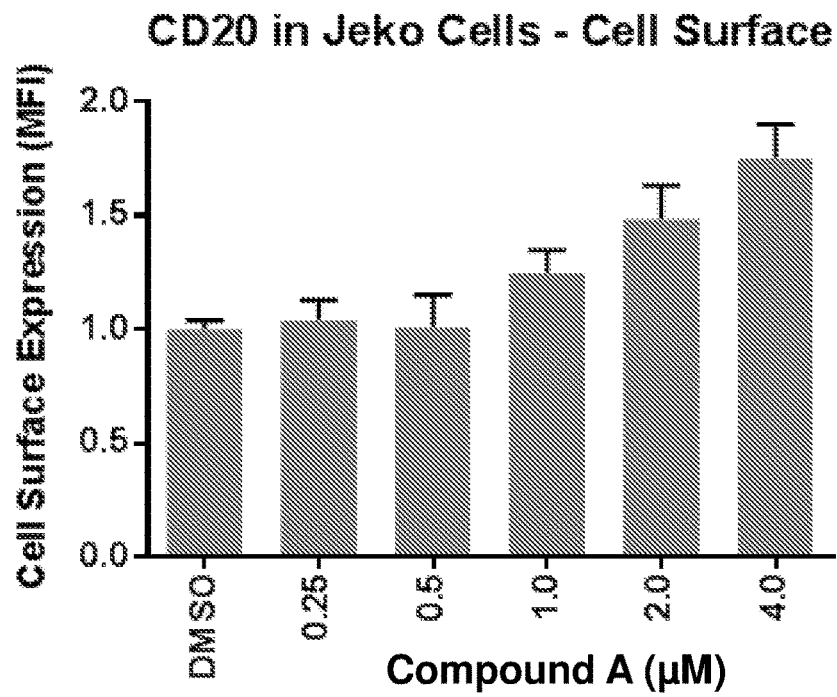
FIG. 3B shows the quantification of mean fluorescence intensity following cell surface staining and flow cytometry showing the levels of CD20 in Jeko cells.
Figure 3C:
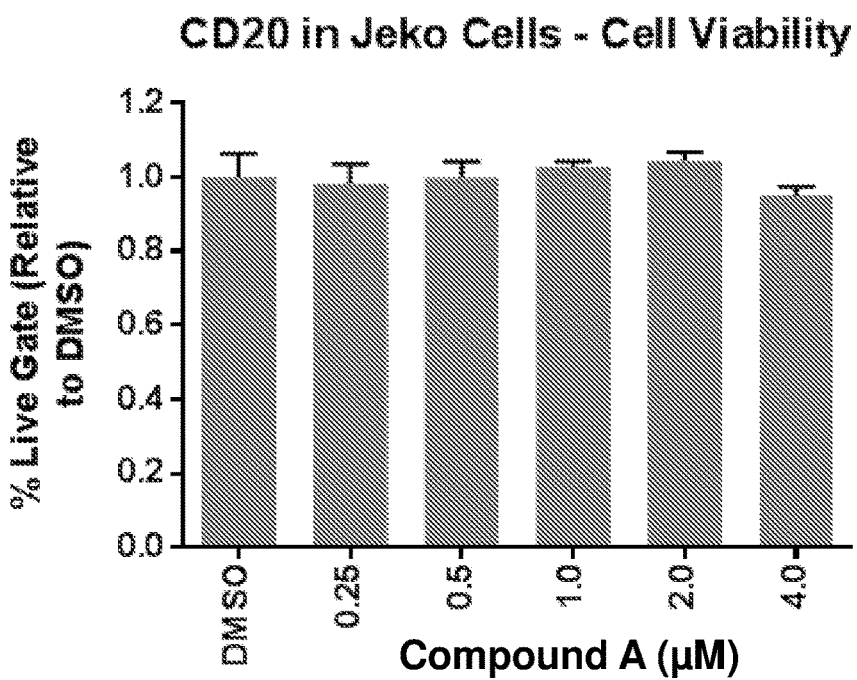
FIG. 3C shows the percentage of live cells as determined by fraction of total cells that were negative for the live/dead viability dye in Jeko cells.
Figure 3D:
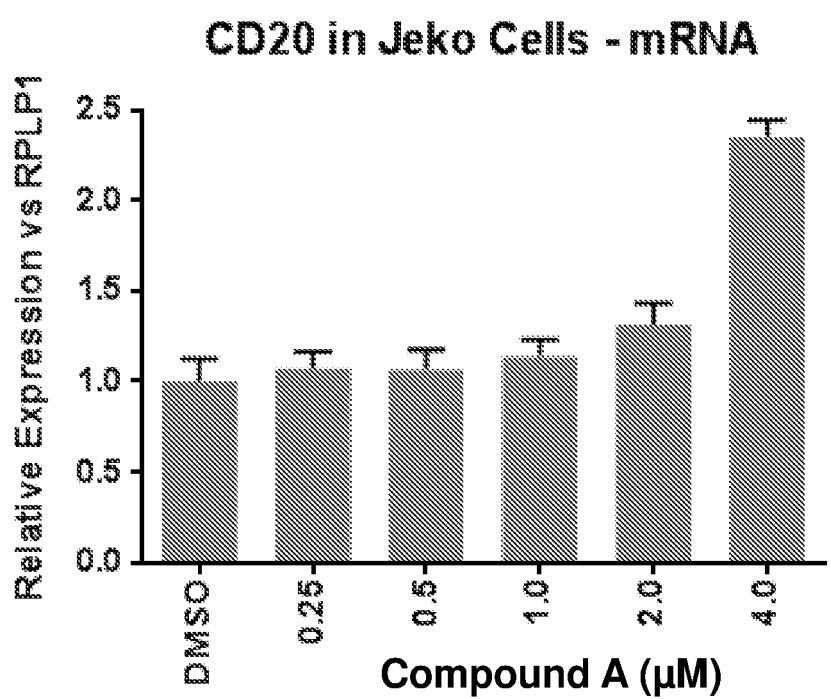
FIG. 3D shows the CD20 mRNA expression relative to RPLP1 in Jeko cells.

Cells were treated with increasing concentrations of Compound A (i.e., 0.25 µM, 0.5 µM, 1.0 µM, 2.0 µM, and 4.0 µM) for 48 hours and processed for cell surface abundance of CD20 protein and mRNA in Jeko cells. The treated Jeko cells were stained for IgG2bK-APC and CD20-APC. FACS histogram plots of a representative sample in Jeko cells for each concentration are shown in FIG. 3A. The dotted line indicates median of DMSO treatment. The quantification of mean fluorescence intensity (MFI) following cell surface staining and flow cytometry of Jeko cells is shown in FIG. 3B. Each sample was background subtracted, where the IgG2bK-APC median MFI in Jeko cells was used as the background. FIG. 3C shows the cell viability as measured by percentage of cells in live gate, relative to DMSO in Jeko cells. FIG. 3D shows CD20 mRNA expression relative to RPLP1 in Jeko cells. Compound A induced CD20 mRNA expression and cell surface abundance of CD20 on Jeko cells. That can be a potential mechanism for the synergistic effect of Compound A with rituximab.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

What is claimed is:

1. A pharmaceutical combination comprising a therapeutically effective amount of:
   a) an HDAC6 selective inhibitor, wherein the HDAC6 selective inhibitor is

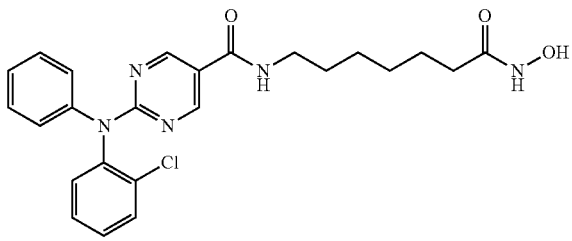 [SMILES: O=C(CCCCCCNC(=O)c1cnc(N(c2ccccc2)c2ccccc2Cl)nc1)NO]

or a pharmaceutically acceptable salt thereof; and
   b) a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

2. The pharmaceutical combination of claim 1, wherein the combination further comprises one or more pharmaceutically acceptable carriers.

3. A method of treating a hematologic malignancy in a subject in need thereof, comprising administering to the subject a therapeutically effective amount of:
   a) a histone deacetylase 6 (HDAC6) selective inhibitor, wherein the HDAC6 selective inhibitor is

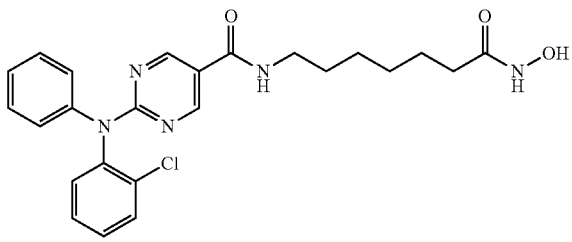 [SMILES: O=C(CCCCCCNC(=O)c1cnc(N(c2ccccc2)c2ccccc2Cl)nc1)NO]

or a pharmaceutically acceptable salt thereof; and
   b) a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab;
   wherein the method comprises upregulating the expression of CD20 in a cell.

4. The method of claim 3, wherein the HDAC6 selective inhibitor and the CD20 inhibitory antibody are together formulated as a single formulation.

5. The method of claim 3, wherein the HDAC6 selective inhibitor and the CD20 inhibitory antibody are each formulated as separate formulations.

6. The method of claim 5, wherein the HDAC6 selective inhibitor is administered orally, and the CD20 inhibitory antibody is administered intravenously.

7. The method of claim 3, wherein the HDAC6 selective inhibitor and the CD20 inhibitory antibody are administered at the same time.

8. The method of claim 3, wherein the HDAC6 selective inhibitor and the CD20 inhibitory antibody are administered at different times.

9. The method of claim 8, wherein the HDAC6 selective inhibitor is administered orally, and the CD20 inhibitory antibody is administered intravenously.

10. The method of claim 3, wherein the cancer is resistant or refractory to treatment with the CD20 inhibitory antibody.

11. The method of any one of claim 3, wherein the hematologic malignancy is selected from the group consisting of acute lymphoblastic leukemia, B-cell leukemia, chronic lymphocytic leukemia, acute myeloid leukemia, chronic myeloid leukemia, B-cell lymphoma, Burkitt lymphoma, diffuse large B-cell lymphoma, non-Hodgkin's lymphoma, lymphocyte predominant subtype of Hodgkin's lymphoma, mantle cell lymphoma, and multiple myeloma.

12. A method of treating a B-cell disorder in a subject in need thereof, comprising administering to the subject a therapeutically effective amount of:
   a) an HDAC6 selective inhibitor, wherein the HDAC6 selective inhibitor is

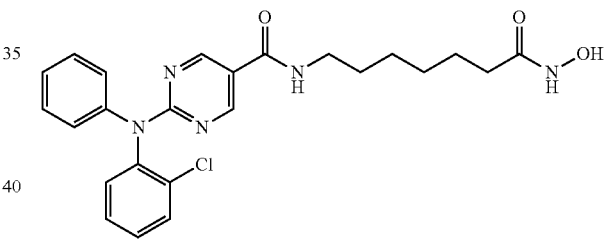

or a pharmaceutically acceptable salt thereof; and
   b) a CD20 inhibitory antibody selected from the group consisting of FBTA05, MT-3724, obinutuzumab, ocaratuzumab, ocrelizumab, ofatumumab, PRO131921, rituximab, SBI-087, TRU-015, ublituximab, and veltuzumab.

13. The method of claim 12, wherein the B-cell disorder is selected from the group consisting of cancer, an autoimmune disorder, and transplant rejection.

* * * * *

UNITED STATES PATENT AND TRADEMARK OFFICE
CERTIFICATE OF CORRECTION

| | | |
|---|---|---|
| PATENT NO. | : 11,324,744 B2 | Page 1 of 1 |
| APPLICATION NO. | : 15/670743 | |
| DATED | : May 10, 2022 | |
| INVENTOR(S) | : Simon Steward Jones | |

It is certified that error appears in the above-identified patent and that said Letters Patent is hereby corrected as shown below:

On the Title Page

At the first and second Line under "OTHER PUBLICATIONS" of Column 2, should read:
Abstract of Hamlin et al, Blood, Dec. 2015, vol. 126, No. 23 (Year: 2015).*

In the Claims

Claim 11, at Lines 18 through 25 of Column 94, should read:
The method of claim 3, wherein the hematologic malignancy is selected from the group consisting of acute lymphoblastic leukemia, B-cell leukemia, chronic lymphocytic leukemia, acute myeloid leukemia, chronic myeloid leukemia, B-cell lymphoma, Burkitt lymphoma, diffuse large B-cell lymphoma, non-Hodgkin's lymphoma, lymphocyte predominant subtype of Hodgkin's lymphoma, mantle cell lymphoma, and multiple myeloma.

Signed and Sealed this
Twenty-sixth Day of September, 2023

Katherine Kelly Vidal
*Director of the United States Patent and Trademark Office*